United States Patent

Khanna et al.

[11] Patent Number: 5,334,717
[45] Date of Patent: Aug. 2, 1994

[54] INTERMEDIATES FOR 2-AMINO AND AZIDO DERIVATIVES OF 1,5-IMINOSUGARS

[75] Inventors: Ish K. Khanna, Vernon Hills; Richard A. Mueller, Glencoe; Richard M. Weier, Lake Bluff, all of Ill.

[73] Assignee: G. D. Searle & Co., Skokie, Ill.

[21] Appl. No.: 2,380

[22] Filed: Jan. 8, 1993

Related U.S. Application Data

[62] Division of Ser. No. 861,696, Apr. 1, 1992, Pat. No. 5,202,251.

[51] Int. Cl.⁵ .................................. C07D 491/056
[52] U.S. Cl. ........................................... 546/116
[58] Field of Search ................................. 546/116

[56] References Cited

U.S. PATENT DOCUMENTS

| | | | |
|---|---|---|---|
| 4,182,763 | 1/1980 | Casten et al. | 424/251 |
| 4,533,668 | 8/1985 | Matsumura et al. | 514/321 |
| 4,639,436 | 1/1987 | Junge et al. | 514/24 |
| 4,849,430 | 7/1989 | Fleet et al. | 514/315 |
| 4,871,747 | 10/1989 | Kinst et al. | 514/315 |
| 4,957,926 | 9/1990 | Jacob et al. | 514/315 |
| 5,003,072 | 3/1991 | Partis et al. | 546/243 |
| 5,011,829 | 4/1991 | Hirsch et al. | 514/50 |
| 5,025,021 | 6/1991 | Getman et al. | 514/302 |
| 5,026,713 | 6/1991 | Getman et al. | 514/302 |
| 5,030,638 | 7/1991 | Partis et al. | 514/315 |

FOREIGN PATENT DOCUMENTS 298350 1/1989 European Pat. Off. .
8703903 7/1987 PCT Int'l Appl. .

OTHER PUBLICATIONS

Fleet, Chem. Lett. 7, 1051–1054 (1986).
Kiso, J. Carbohydr. Chem. 10, 25–45 (1991).

*Primary Examiner*—Bernard Dentz
*Attorney, Agent, or Firm*—Scott J. Meyer

[57] ABSTRACT

Novel derivatives of 1-deoxynojirimycin are disclosed which have amino or azido substituents at C-2 and/or C-3. These compounds are useful inhibitors of lentiviruses. Methods of chemical synthesis of these derivatives and intermediates therefor are also disclosed.

2 Claims, No Drawings

INTERMEDIATES FOR 2-AMINO AND AZIDO DERIVATIVES OF 1,5-IMINOSUGARS

This is a division of application Ser. No. 07/861,696, filed Apr. 1, 1992 now U.S. Pat. No. 5,202,251.

BACKGROUND OF THE INVENTION

This invention relates to novel derivatives of 1,5-dideoxy-1,5-imino-D-glucitol having amino or azido substituents at C-2 and/or C-3, and, more particularly, to the chemical synthesis of these derivatives and intermediates therefor, and to their method of inhibiting viruses such as lentiviruses.

1,5-dideoxy-1,5-imino-D-glucitol (deoxynojirimycin or DNJ) and its N-alkyl and O-acylated derivatives are known inhibitors of viruses such as human immunodeficiency virus (HIV). See, e.g., U.S. Pat. Nos. 4,849,430; 5,003,072; 5,030,638 and PCT Int'l. Appln. WO 87/03903. Several of these derivatives also are effective against other viruses such as HSV and CMV as disclosed in U.S. Pat. No. 4,957,926. In some cases antiviral activity is enhanced by combination of the DNJ derivative with other antiviral agents such as AZT as described in U.S. Pat. No. 5,011,829. Various of these DNJ derivative compounds are antihyperglycemic agents based on their activity as glycosidase inhibitors. See, e.g., U.S. Pat. Nos. 4,182,763, 4,533,668 and 4,639,436. The 2-acetamide derivatives of DNJ also are reported to be potent glycosidase inhibitors by Fleet et al., *Chem. Lett.* 7, 1051–1054 (1986); and Kiso et al. *J. Carbohydr. Chem.* 10, 25–45 (1991).

Notwithstanding the foregoing, the search continues for the discovery and novel synthesis of new and improved antiviral compounds.

BRIEF DESCRIPTION OF THE INVENTION

In accordance with the present invention, novel derivatives of 1,5-dideoxy-1,5-imino-D-glucitol having amino or azido substituents at C-2 and/or C-3 are provided. According to another embodiment of the invention, novel methods of chemical synthesis of these DNJ derivatives and their intermediates are provided. The novel DNJ derivatives and various of their intermediates have useful antiviral activity as demonstrated against lentivirus.

The novel C-2 and/or C-3 amino or azido substituted derivatives of 1,5-dideoxy-1,5-imino-D-glucitol can be represented by the following general structural Formula I:

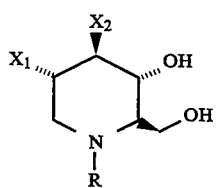

(I)

wherein $R = H$, alkyl, and aralkyl;
$X_1 = OH$, $N_3$, $NH_2$, $NHR_1$, $NR_2$ and $NHCOR_3$;
$X_2 = OH$, $N_3$ and $NH_2$, provided that when $X_2$ is $N_3$ or $NH_2$, $X_1$ is OH or $NH_2$, and provided further that at least one of $X_1$ and $X_2$ is not OH;
$R_1$, $R_2$ = alkyl; and
$R_3 = H$, alkyl.

In Formula I, the alkyl moieties in the R, $R_1$, $R_2$ and $R_3$ substituents preferably are straight chain or branched alkyl groups or cycloalkyl groups which preferably have from one to about 8 carbon atoms in $R_1$, $R_2$ and $R_3$, e.g., methyl, ethyl, propyl, isopropyl, n-butyl, iso-butyl, sec.-butyl. tert-butyl, pentyl, hexyl, heptyl, octyl, 2-ethylbutyl, 2-methylpentyl, cyclopentyl and cyclohexyl, and from one to about 18 carbon atoms in R, e.g., dodecyl, octadecyl or any of the above groups.

Also in Formula I, the aryl moieties in the R substituents preferably are phenyl and substituted phenyl, e.g. benzyl, 4,fluorophenyl or 3-methoxyphenyl.

Preferred compounds of Formula I are the following:

2-Azido Derivatives of DNJ

2-Azido-1,2,5-trideoxy-1,5-imino-D-glucitol
2-Azido-1,5-(butylimino)-1,2,5-trideoxy-D-glucitol
2-Azido-1,5-[(2-ethylbutyl)imino]-1,2,5-trideoxy-D-glucitol
2-Azido-1,5-[(4,4,4-trifluorobutyl)imino]-1,3,5-trideoxy-D-glucitol

2-Amino Derivatives of DNJ

2-Amino-1,2,5-trideoxy-1,5-imino-D-glucitol
2-Amino-1,5-(butylimino)-1,2,5-trideoxy-D-glucitol
2-Amino-1,5-[(2-ethylbutyl)imino]-1,2,5-trideoxy-D-glucitol
2-Amino-1,5-[(4,4,4-trifluorobutyl)imino]-1,2,5-trideoxy-D-glucitol
1,5-(Butylimino)-1,2,5-trideoxy-2-(dimethylimino)-D-glucitol
1,5-(Butylimino)-1,2,5-trideoxy-2-(methylamino)-D-glucitol
1,5(Butylimino)-1,2,5-trideoxy-2-[(1-oxobutyl)amino]-D-glucitol
1,5(Burylimino)-1,2,5-trideoxy-2-[(1-oxobutyl)amino]-D-glucitol, tributanoate

3-Amino Derivatives of DNJ

3-Amino-1,3,5-trideoxy-1,5-imino-D-glucitol
2,3-Diamino-1,5-(butylimino)-1,2,3,5-tetradeoxy-D-glucitol The novel synthesis of compounds of Formula I comprises the formation of structural modifications at C2 and C3 of DNJ and the nucleophilic opening of N-carboalkoxy-2,3-anhydro-DNJ.

In accordance with a preferred embodiment of the invention, the compounds of Formula I can be chemically synthesized by the sequence of reactions shown in the following generic Reaction Schemes A, D and F in which the Roman numerals in parentheses refer to the compounds defined by the generic formula shown above said numbers. $R_1$ can be any alkyl or aryl group such as illustrated by the reactants and products described hereinafter.

Scheme A:
Generic Synthesis of 2-azido and 2-amino 1,5-iminosugars.

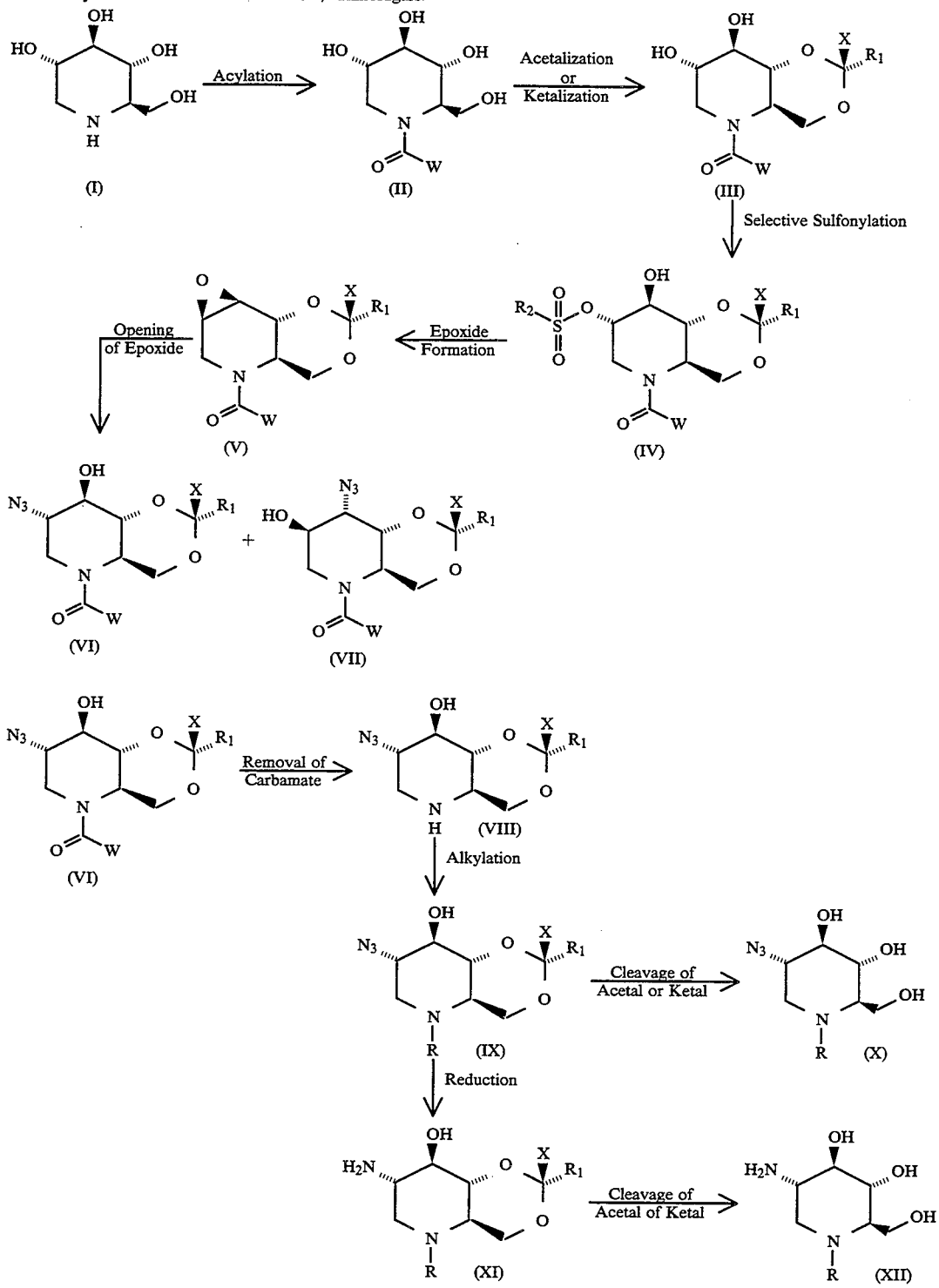

The foregoing Reaction Scheme A comprises the following general reaction steps:

(a) The starting material, DNJ (I), is N-acylated with an acylating agent to form a carbamate derivative of DNJ (II);

(b) The hydroxyls at C-4 and C-6 are protected with a hydroxyl protecting agent by acetalization or ketalization to form an acetal or ketal (III);

(c) The hydroxyl at C-2 is protected by regioselective sulfonylation with a sulfonylating agent at C-2 to give the 2-sulfonated intermediate (IV);

(d) A 2,3-anhydro derivative is formed by epoxidation at C-2 and C-3 to give the epoxide intermediate (V);

Epoxide intermediate (V) is used for synthesis of 2-azido and 2-amino derivatives of DNJ in the following steps of Reaction Scheme A or retained for synthesis of 3-amino derivatives of 1,5-imino-D-altritol in Reaction Scheme H.

(e) The epoxide intermediate (V) is opened by nucleophilic attack at C-2 and C-3 such as with an azide to give a mixture of azido derivatives (VI) and (VII);

Azido derivative (VII) is retained for synthesis of 3-azido and 3-amino derivatives of DNJ in Reaction Scheme D.

Azido derivative (VI) is used for synthesis of 2-azido and 2-amino derivatives of DNJ in the following steps of Reaction Scheme A or retained for synthesis of 2,3-diamino derivatives of DNJ in Reaction Scheme F.

(f) The N-carbamate group in azido derivative (VI) is removed to give intermediate (VIII).

(g) Intermediate (VIII) is N-alkylated to give the divergent intermediate (IX) which can be used to prepare the final 2-azido or 2-amino derivatives of DNJ.

(h) The hydroxyl protecting group at C-4 and C-6 of intermediate (IX) is removed by cleavage of acetal or ketal to give the desired novel antiviral 2-azido derivatives of DNJ (X), (i) The 2-azido group in intermediate (IX) is reduced to the 2-amino group to give intermediate (XI);

(j) The hydroxyl protecting group at C-4 and C-6 of intermediate (XI) is removed by cleavage of acetal or ketal to give the desired novel antiviral 2-amino derivatives of DNJ (XII).

N-Acylation of DNJ (I) in step (a) can be carried out by conventional N-acylation procedures well known to those skilled in the art. Suitable general procedures for acylation of amines are described in U.S. Pat. No. 5,003,072; March, J. in *Advanced Organic Chemistry*, Wiley, New York, 1985; Patai, S. (Ed.) in *The Chemistry of Amides*, Wiley, New York, 1970. For example, DNJ is N-acylated to form carbamate or thiocarbamate using a variety of reagents such as chloroformates (e.g., methyl chloroformate, ethyl chloroformate, vinyl chloroformate, benzyl chloroformate) or dicarbonates (e.g., di-tertbutyl dicarbonate). The reaction of DNJ (I) with anhydrides, chloroformates or dicarbonates is preferentially carried out by dissolving in one or more of polar, protic solvents (such as water, methanol, ethanol) and in the presence of a base (e.g, potassium carbonate, lithium carbonate, sodium carbonate, cesium carbonate, triethylamine, pyridine, 4-dimethylaminopyridine, diisopropylethylamine, 1,8-diazabicyclo[5,4,0]undec-7-ene). N-Acylation is preferentially carried out by reacting DNJ (I) with alkyl or aryl chloroformate in solvents such as DMF or aqueous sodium bicarbonate at 20°-50° C. to give the product (II).

Protection of the hydroxyl groups at C-4 and C-6 in step (b) to give acetal or ketal derivative (III) can be carried out by conventional hydroxyl protection procedures such as those described, e.g., in U.S. Pat. No. 5,003,072 and in Green, T. W., *Protective Groups in Organic Synthesis*, Wiley, New York, 1981. The cyclic acetals and ketals are formed by the reaction of 4,6-dihydroxy compound (II) with an aldehyde or a ketone in the presence of an acid catalyst. Illustrative carbonyl (or carbonyl equivalents such as dimethyl acetal or dimethyl ketal) compounds useful in this reaction are acetone, acetaldehyde, methyl phenyl ketone, benzaldehyde, 4-methoxybenzaldehyde, 2,4-dimethoxybenzaldehyde, 4-dimethylaminobenzaldehyde, 2-nitrobenzaldehyde, 2,2,2-trichloroacetaldehyde (chloral) and acetophenone. The acid catalysts suitable for this reaction are, e.g., para-toluene sulfonic acid, cat. HCl, cat. sulfuric acid, $FeCl_3$, $ZnCl_2$, $SnCl_2$ and $BF_3$-ether, and the reaction is carried out in the presence of aprotic solvents such as methylene chloride, 1,2-dimethoxyethane, dioxane, dimethylformamide, dimethylacetamide or dimethylsulfoxide. Thus paratoluene sulfonic acid is added to a solution of benzaldehyde dimethyl acetal in organic medium, e.g., dimethylformamide, and reacted with N-acyl-DNJ (II) at 20°-65° C. to give the product (III).

The selective protection of the hydroxy group at C-2 in compound (III) in step (c) can be carried out by regioselective tosylation to give the tosylate (IV). For example, compound (III) is conveniently refluxed with dibutyltinoxide in solvents (such as benzene, toluene, xylene, methanol or ethanol and the like) to form a homogeneous solution. The stannylene intermediate is then reacted with p-toluenesulfonyl chloride to give tosylate (IV). Other sulfonyl chlorides such as benzenesulfonyl chloride, 4-bromobenzenesulfonyl chloride, 4-nitrobenzenesulfonyl chloride and methanesulfonyl chloride can also be used in this reaction.

The epoxide intermediate (V) is readily prepared in step (d) by treatment of the sulfonate (IV) with base such as sodium hydride, potassium hydride, lithium hydride, cesium carbonate, potassium carbonate and potassium tert-butoxide using solvents such as dimethylformamide, dimethylacetamide, dimethylsulfoxide, dimethoxyethane, tetrahydrofuran, dioxane, diethyl ether, dibutyl ether and tert-butyl methyl ether.

The nucleophilic opening of epoxide intermediate (V) in step (e) is preferably carried out by heating (50° C.-reflux) a solution of (V) in solvents such as dimethylformamide, dimethylacetamide, 2-methoxyethanol, dimethoxyethane, tetrahydrofuran, dioxane, dibutl ether and tert-butyl methyl ether with sodium azide to give diasteromeric mixture of the products (VI) and (VII).

The nitrogen protecting carbamate group in compound (VI) can be easily removed in step (f) by base hydrolysis at temperature of 40° to 100° C. to give the intermediate (VIII). Illustrative bases suitable for this reaction are aqueous sodium hydroxide, lithium hydroxide or potassium hydroxide with or without the presence of organic solvents such as methanol, ethanol, ethylene glycol and dioxane. The carbamates can also be cleaved by other reagents such as sulfur nucleophiles (e.g., sodium thiomethoxide and lithium thiopropoxide) or iodotrimethylsilane.

N-Alkylation of intermediate (VIII) can be carried out in step (g) by reductive alkylation procedures using $NaCNBH_3$, $NaBH_4$ or alkylaldehyde. Appropriate alkylaldehydes for preparing the corresponding N-alkyl derivative compounds (IX) are, e.g., n-propanal, n-butanal, n-pentanal, n-hexanal, n-heptanal and n-octanal. Preferred aldehydes for this reaction are, e.g., butyraldehyde, 3-phenylpropionaldehyde and 2-ethylbutyraldehyde.

Alternatively, N-alkylation can be achieved by reacting intermediate (VIII) with alkylhalide such as benzyl bromide, bromobutane, bromohexane, iodomethane and the like in the presence of a base such as triethylamine, pyridine and diisopropylethylamine. Suitable solvents for the reaction are, e.g., DMF, dimethylacetamide, dimethylsulfoxide and pyridine. A preferred alkylhalide for the N-alkylation is 1-bromo-4,4,4-trifluorobutane.

The acetal or ketal group from the intermediate (IX) can be removed by acid catalyzed hydrolysis in step (h) to give the novel 2-azido derivatives of DNJ (X). Acids can be used such as trifluoacetic acid (with or without water), aqueous hydrochloric acid, boron trichloride, 1N sulfuric acid, 80% acetic acid, with acidic resin (such as Dowex 50-W, H+), catalytic p-toluenenesulfonic acid in methanol or ethanol at 25°–80° C. The benzylidine acetal can also be cleaved using N-bromosuccinimide and BaCO₃ (or CaCO₃) in carbon tetrachloride or by electrochemical reduction.

Reduction of the 2-azido group in intermediate (IX) to give the 2-amino intermediate (XI) in step (i) is conveniently carried out by hydrogenation with palladium on carbon. The acetal or ketal group can then be removed from intermediate (XI) in step (j) by using conditions similar to those elaborated in step (h) to give the novel 2-amino derivatives (XII) of DNJ. When the 4,6-hydroxy protecting group in (XI) is benzylidine acetal, the group may be removed by transfer hydrogenation conditions (e.g., heating a solution of (XI) in ethanol with Pd(OH)₂ and hydrogen donors such as cyclohexene or 1,4-cyclohexadiene). The benzylidine group in (XI) can similarly be removed by using metals (such as Li, Na or K) and liquid ammonia at −70° to −33° C. to give (XII). The benzylidine acetal can also be cleaved using N-bromosuccinimide and BaCO₃ (or CaCO₃) in carbon tetrachloride or by electrochemical reduction. 2,2,2-Trichloroethylidine acetal can also be cleaved by catalytic reduction (H₂, Raney Ni) using aqueous sodium hydroxide and ethanol.

The following Reaction Schemes B and C show the preferred synthesis of, respectively, the 2-azido and 2-amino derivatives of DNJ (Scheme B) and the 2-alkylamino and 2-acylamino derivatives of DNJ (Scheme C), in which the arabic numerals in parentheses refer to compounds prepared in detailed Examples set forth hereinbelow:

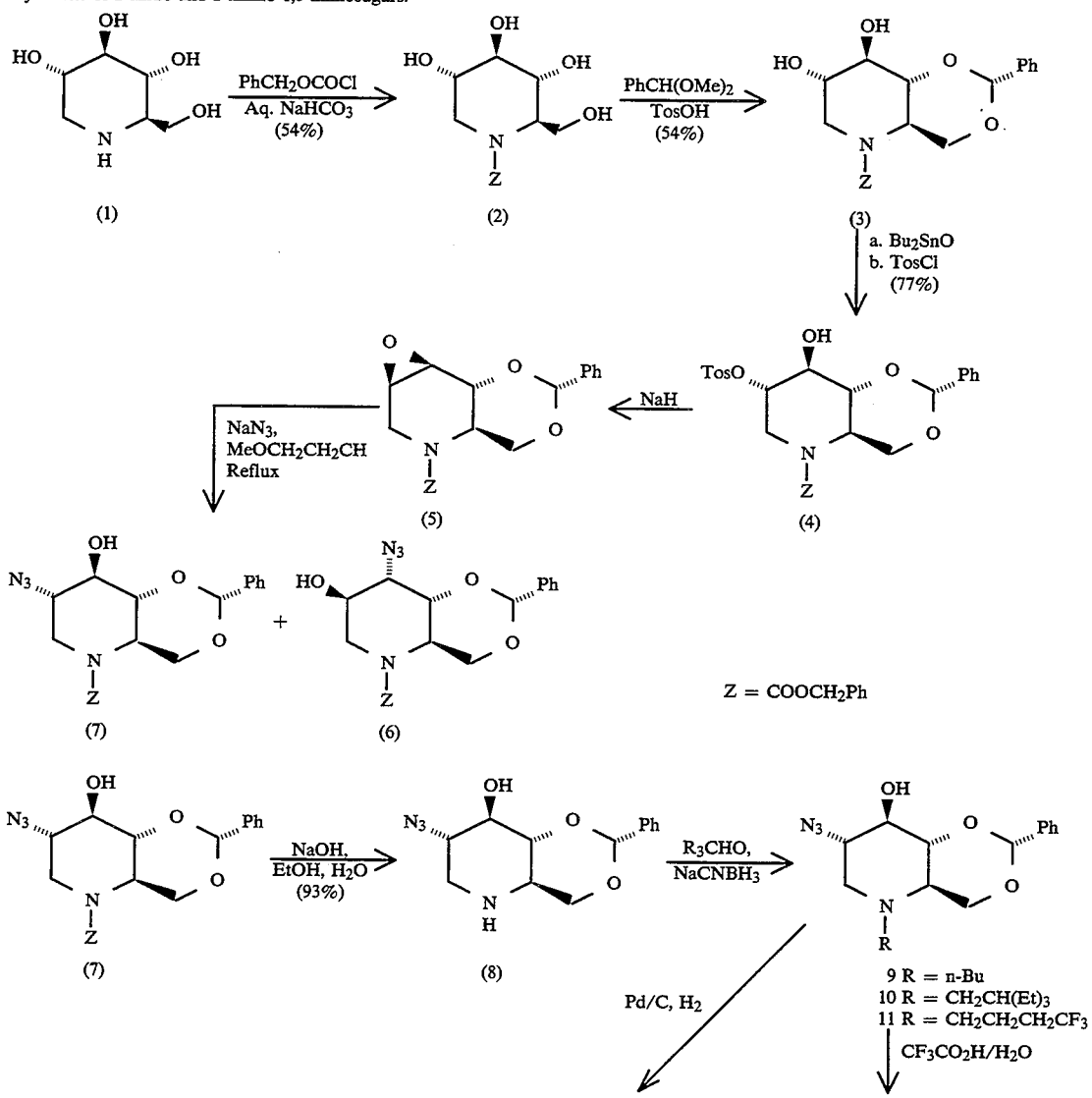

Scheme B:
Synthesis of 2-azido and 2-amino 1,5-iminosugars.
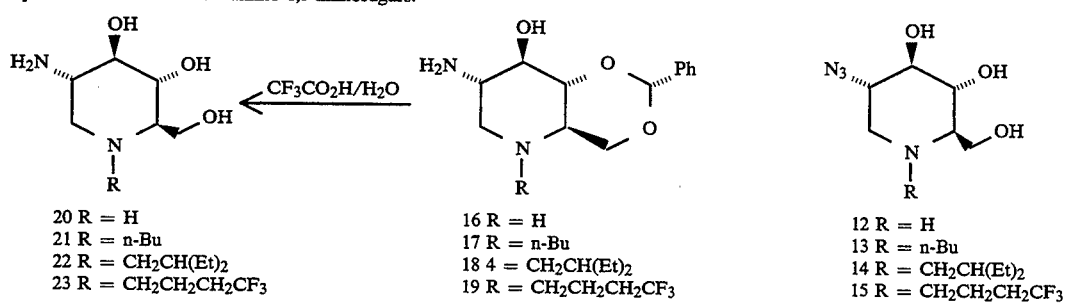
20 R = H
21 R = n-Bu
22 R = CH2CH(Et)2
23 R = CH2CH2CH2CF3
16 R = H
17 R = n-Bu
18 4 = CH2CH(Et)2
19 R = CH2CH2CH2CF3
12 R = H
13 R = n-Bu
14 R = CH2CH(Et)2
15 R = CH2CH2CH2CF3
Scheme C:
Synthesis of 2-alkylamino & 2-acylamido 1,5-iminosugars.
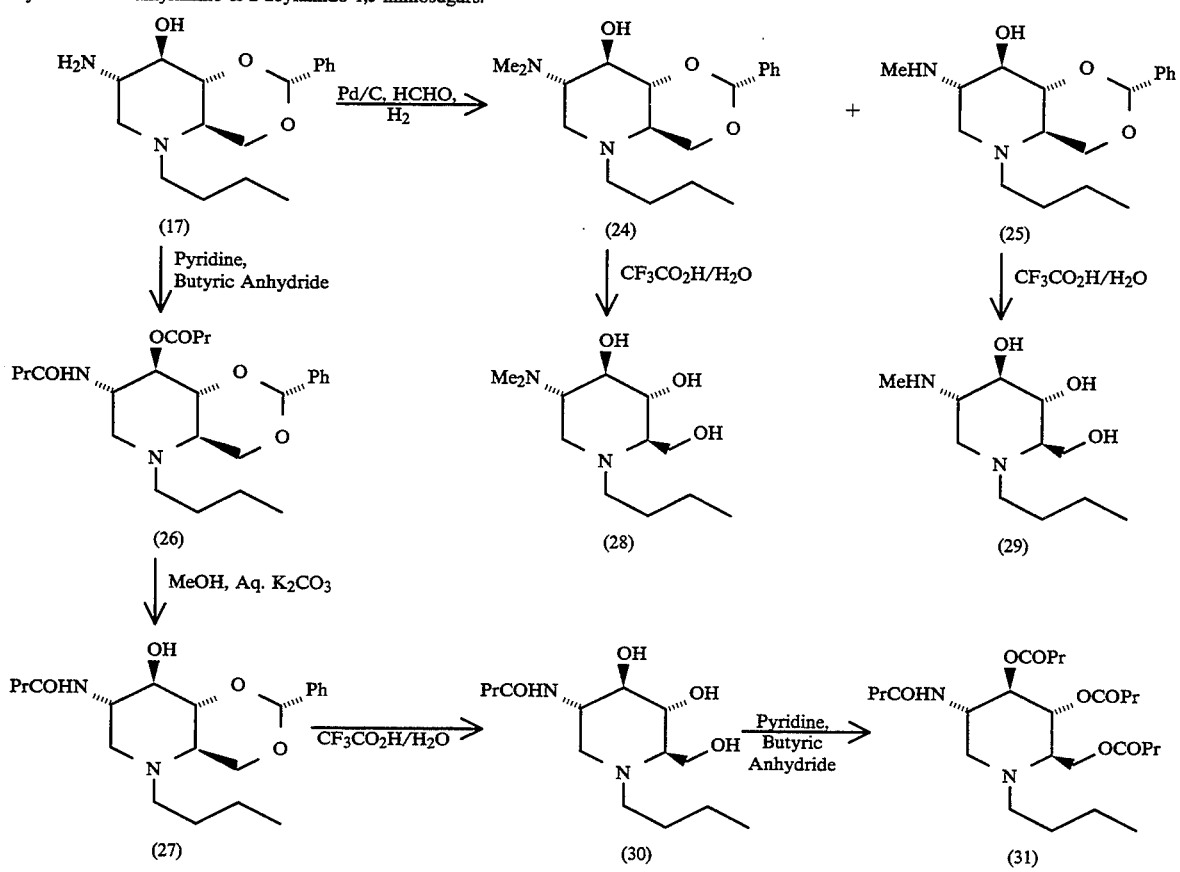
Scheme D:
Generic Synthesis of 3-azido & 3-amino-1,5-iminosugar
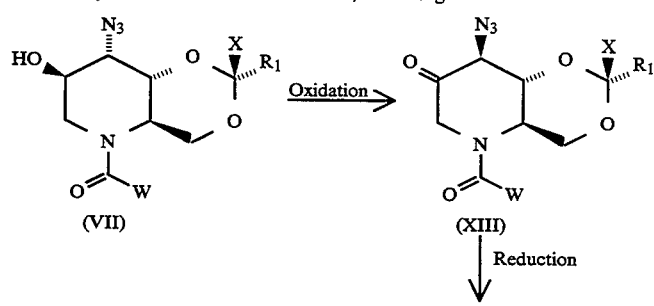

Scheme D:
Generic Synthesis of 3-azido & 3-amino-1,5-iminosugar

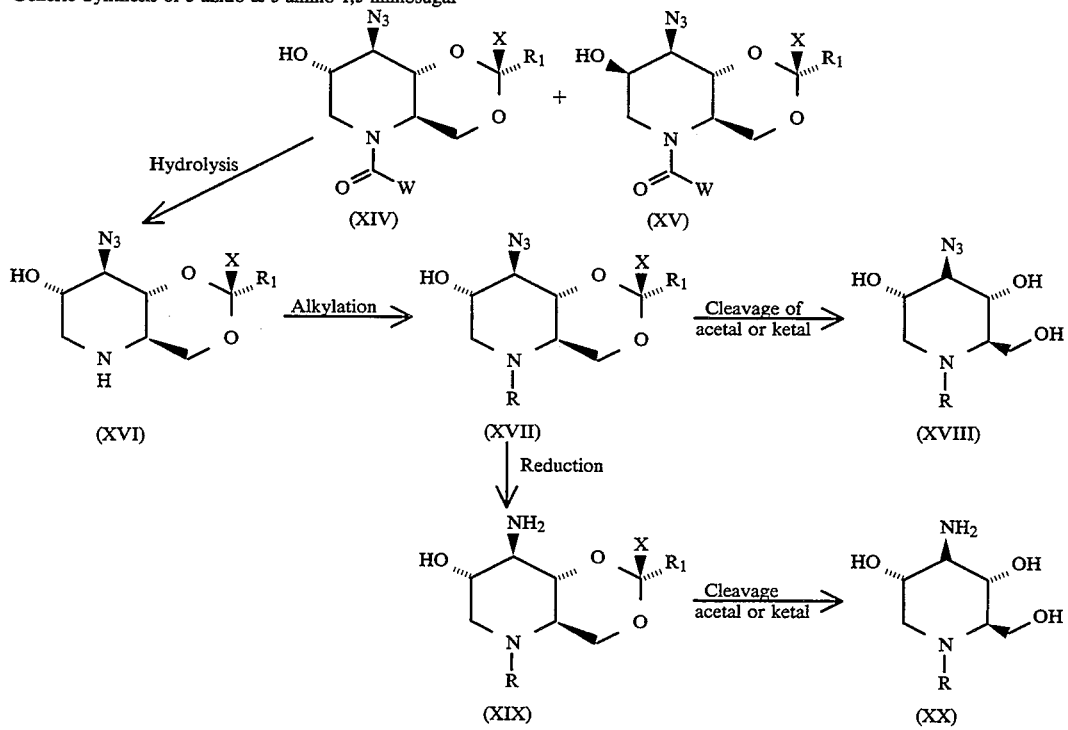

The foregoing Reaction Scheme D, which shows the generic synthesis of the 3-azido- and 3-amino-DNJ derivatives of Formula I, comprises the following general reaction steps, starting with azido derivative (VII) which was prepared in step (e) of Reaction Scheme A:

(a) The free hydroxyl group at C-2 in the starting material, azido derivative (VII), is oxidized to give ketone (XIII);

(b) The ketone (XIII) is reduced with a reducing agent such as, e.g., diisobutylaluminum hydride, sodium borohydride and the like, to give the mixture of epimeric alcohols (XIV) and (XV);

(c) The N-carbamate in alcohol (XIV) is hydrolytically cleaved to give intermediate (XVI);

(d) Intermediate (XVI) is N-alkylated to give divergent intermediate (XVII) which can be used to prepare the final 3-azido or 3-amino derivatives of DNJ;

(e) The hydroxyl protecting group at C-4 and C-6 of intermediate (XVII) is removed by cleavage of acetal or ketal to give the desired 3-azido derivatives of DNJ (XVIII);

(f) The 3-azido group in intermediate (XVII) is reduced to the 3-amino group to give intermediate (XIX);

(g) The hydroxyl protecting group at C-4 and C-6 of intermediate (XIX) is removed by cleavage of acetal or ketal to give the desired 3-amino derivatives of DNJ (XX).

In the foregoing Reaction Scheme D, steps (c) through (g) for the synthesis of the 3-azido and 3-amino derivatives of DNJ can be carried out with similar reagents and conditions in a manner analogous to steps (f) through (j) used for the synthesis of the 2-azido and 2-amino derivatives of DNJ in Reaction Scheme A. In step (a), since the rest of the molecule is fully protected, the oxidation of secondary alcohol in (VII) can be successfully carried out by a variety of oxidizing agents. (see, e.g., March, J. in *Advanced Organic Chemistry*, Wiley, New York, 1985; House, H.O. in *Modern Synthetic Reactions*, Benzamin Publishing Co., Massachusetts, 1972; Augusting, R. L. in *Oxidations—Techniques and Applications in Organic Synthesis*, Dekker, New York, 1969; W. P. Griffith and S. M. Levy, *Aldrichchimica Acta* 23, 13 (1990); R. M. Moriarty and O. Prakash *J. Org. Chem.* 50, 151, 1985; A. Mancuso, D. Swern, *Synthesis*, 165 (1981); S. Czernecki, C. Georgoulus, C. L. Stevens and K. Vijayakantam, *Tetrahedron Lett.* 26, 1699 (1985); J. Hersovici, M. J. Egra and K. Antonakis, *J. Chem. Soc. Perkin Trans. I,* 1967 (1982); E. J. Corey, E. Barrette and P. Margriotis, *Tetrahedron Lett.* 26, 5855 (1985); H. Tomioka, K. Oshima and H. Nozaki, *Tetrahedron Lett.* 23, 539 (1982). Some of the reagents suitable for oxidation of the C-2 hydroxyl in compound VII are pyridinium chlorochromate (with or without additives such as sodium acetate, celite, alumina, molecular sieves), pyridinium dichromate, chromium trioxide/pyridine, 2,2'-bipyridinium chloroacromate, cyclic chromate ester (E. J. Corey, E. Barrette and P. Margriotis, *Tetrahedron Lett.* 26, 5855 (1985), RuCl$_2$(PPh$_3$)$_3$-tert-BuOOH, silver carbonate on celite, cerium (IV) ammonium nitrate (with or without sodium bromate), tetra-n-propylammonium perruthenate, activated dimethyl sulfoxide reagents (using DMSO and one of the electrophilic reagents such as acetic anhydride, trifluoroacetic anhydride, oxalyl chloride, trifluorosulfonic anhydride, dicyclohexylcarbodiimide). Formation of the novel carbonyl compound (XIII) is preferentially carried out by oxidation of the hydroxyl group at C-2 (VII) with trifluoroacetic anhydride in dimethylsulfoxide (DMSO) using methylene chloride as solvent at −70° to 0° C. followed by treatment with base such as triethylamine or diisopropylethylamine at −70° to 25° C.

The following Reaction Scheme E shows the preferred synthesis of the 3-amino derivatives of DNJ in which the arabic numerals in parentheses refer to compounds prepared in detailed Examples set forth hereinbelow. Table 1, below, sets forth the results obtained in proportions of alcohols (33) and (34) by the reduction of ketone (32) under various reducing conditions.

TABLE 1

Studies on Stereoselective Reduction of 32

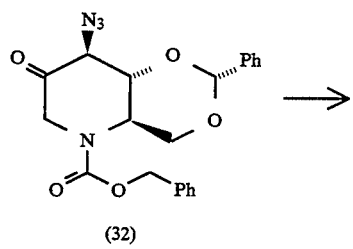

(32)

TABLE 1-continued

| Reducing Agent | Conditions | Relative Yield (33/34) | Chem. Yield (33 + 34, %) |
|---|---|---|---|
| NaBH$_4$ | THF/MeOH (4/1), −15°–0° C., 30 min | 52/48 | 67 |
| LIBH$_3$Me MeLi—LiBr + BH$_3$—Me$_2$S | −70° to −20° C., 3 hr | 37/63 | 20 |
| Me$_3$Al, t-BuMgCl, 2,6-dibutyl-4-methyl phenol | 0–5° C., 5 hr | 85/15 | 26 |
| DIBAL-H (1M soln. in toluene) | −70° C., 4 hr | 86/14 | 86 |

Scheme E:
Synthesis of 3-amino-1,5-iminosugars.

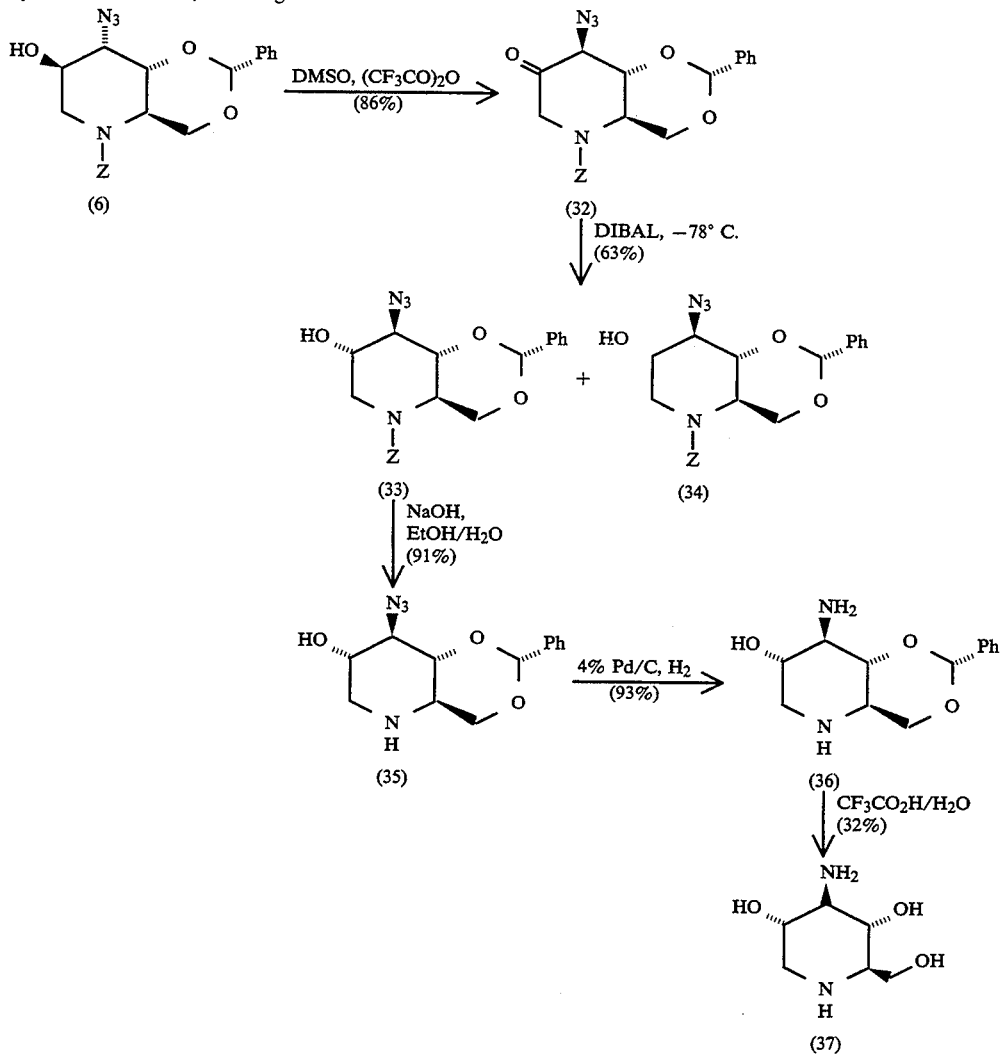

Scheme F:
Generic Synthesis of 2,3-diamino-1,5-iminosugars.

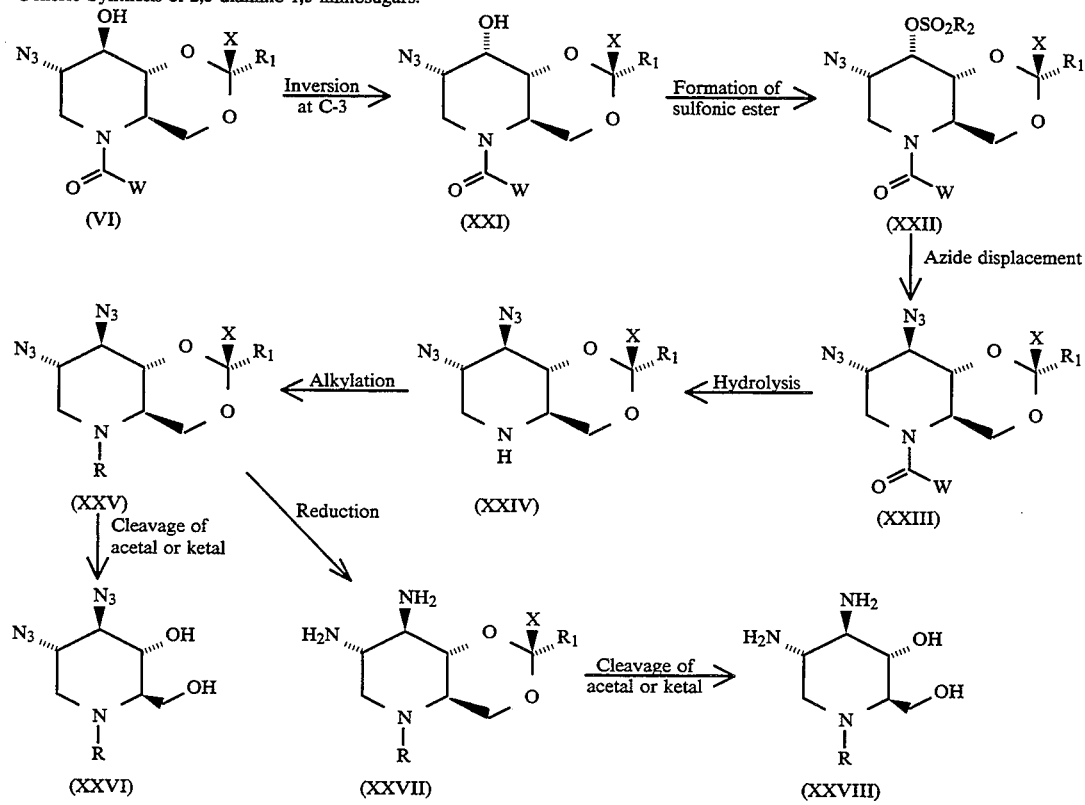

The foregoing Reaction Scheme F, which shows the generic synthesis of the 2,3-diamino-DNJ derivatives of Formula I, comprises the following general reaction steps, starting with azido derivative (VI) which was prepared in step (e) of Reaction Scheme A:

(a) Azido derivative (VI) is subjected to inversion of configuration at C-3 to give the talo intermediate (XXI);

(b) The free hydroxyl at C-3 of intermediate (XXI) is sulfonated to give sulfonic ester (XXII);

(c) Sulfonic ester (XXII) is subjected to azide displacement with inversion to the gluco configuration at C-3 to give diazido intermediate (XXIII);

(d) The N-carbamate in diazido intermediate (XXIII) is hydrolytically cleaved to give intermediate (XXIV);

(e) Intermediate (XXIV) is N-alkylated to give divergent intermediate (XXV) which can be used to prepare the final 2,3-diamino or 2,3-diazido derivatives of DNJ;

(f) The hydroxyl protecting group at C-4 and C-6 of intermediate (XXV) is removed by cleavage of acetal or ketal to give the 2,3-diazido derivatives of DNJ (XXVI);

(g) The 2,3-diazido groups in intermediate (XXV) are reduced to the 2,3-diamino groups to give intermediate (XXVII);

(h) The hydroxyl protecting group at C-4 and C-6 of intermediate (XXVII) is removed by cleavage of acetal or ketal to give the desired 2,3-diamino derivatives of DNJ (XXVIII).

In the foregoing Reaction Scheme F, steps (d) through (h) for the synthesis of the 2,3-diazido and 2,3-diamino derivatives of DNJ can be carried out with similar reagents and conditions in a manner analogous to steps (f) through (j) used for the synthesis of the 2-azido and 2-amino derivatives of DNJ in Reaction Scheme A. Reaction steps (a) through (c) involve displacement of hydroxyl at C-3 by an azide group with net retention of configuration.

The following Reaction Scheme G shows the preferred synthesis of the 2,3-diamino derivatives of DNJ in which the arabic numerals in parenthesis refer to compounds prepared in detailed Examples set forth hereinafter.

Scheme G:
Synthesis of 2,3-diamino-1,5-iminosugars.
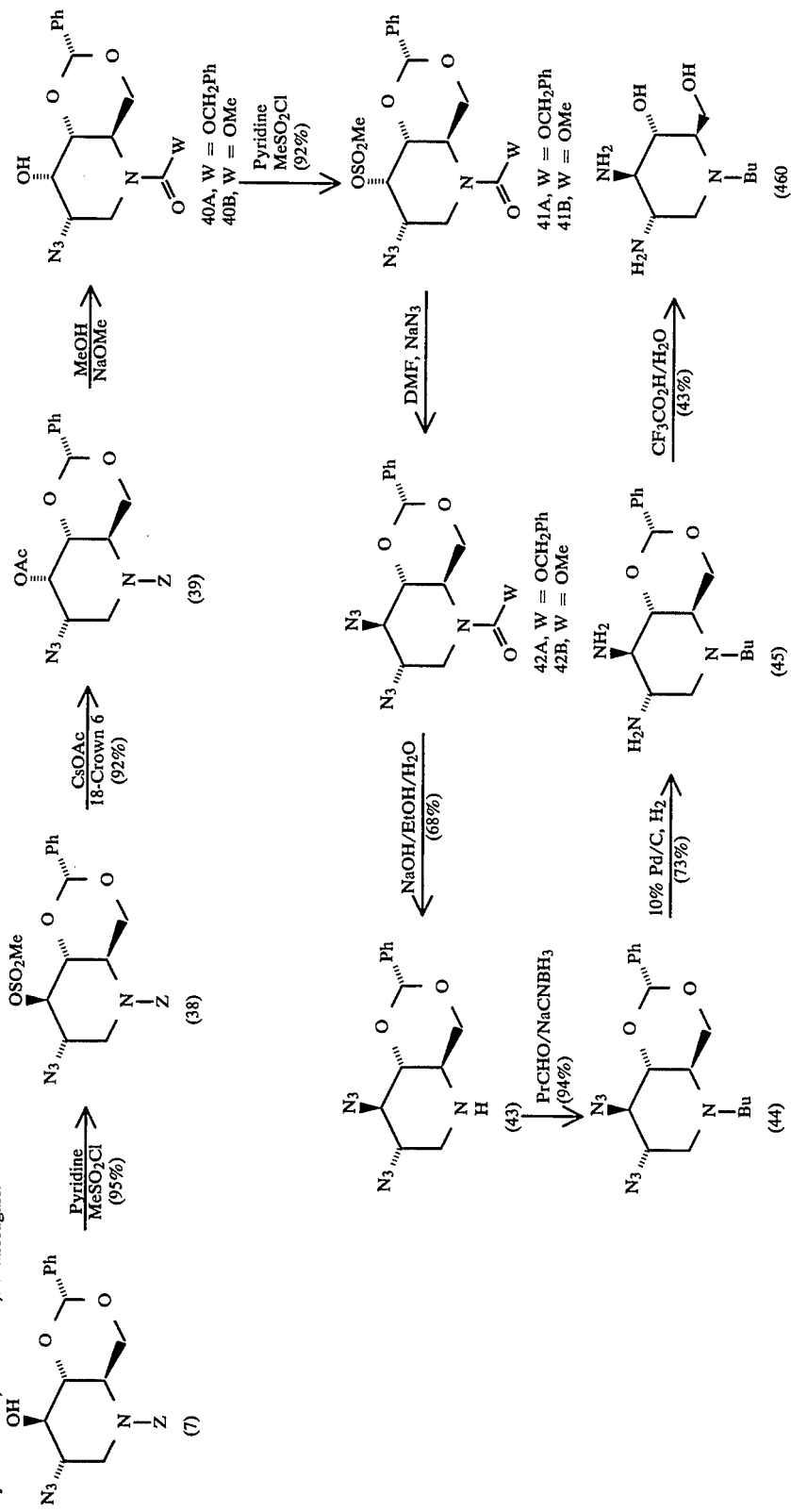

The following Reaction Scheme H shows the synthesis of 3-amino derivatives of 1,5-imino-D-altritol from epoxide intermediate (V) of Reaction Scheme A and, preferably, the epoxide intermediate (5) of Reaction Scheme B. Reaction Scheme H comprises the following reaction steps in which the arabic numerals in parentheses refer to compounds prepared in detailed Examples set forth hereinbelow:

(a) The epoxide intermediate (5) is opened by refluxing in alkylamine such as N,N-dimethylaminoethylamine or butylamine to give the C-4 and C-6 hydroxyl protected 3-amino derivatives of 1,5-imino-altritol (47) and (48), respectively;

(b) The benzyl carbamate (Z) on the 3-amino derivative (47) is removed by base hydrolysis or by catalytic hydrogenation procedures ($H_2$ and Pd/C or $H_2$ and Pd black) to give intermediate (49); and (c) The hydroxyl protecting group at C-4 and C-6 of intermediate (49) is removed by cleavage of acetal or ketal to give the desired novel antiviral 3-amino derivative of 1,5-imino-D-altritol (50). This step can be carried out in a manner analogous to the acid catalysed hydrolysis to remove the acetal or ketal group from intermediate (IX) in step (h) of Reaction Scheme A.

DETAILED DESCRIPTION OF THE INVENTION

The following examples will further illustrate the invention although it will be understood that the invention is not limited to these specific examples or the details disclosed therein.

EXAMPLE 1

Preparation of 1,5-dideoxy-1,5-[{(phenylmethoxy)carbonyl}imino]-D-glucitol (2)

To a stirred solution of 1-deoxynojirimycin (100 g, 0.61 mol) in saturated aqueous sodium bicarbonate (1000 ml), benzyl chloroformate (95%, 121 g, 0.67 mol) was added dropwise at room temperature. After stirring at room temperature for 18 hr, the solution was extracted once with methylene chloride (300 ml) to remove any unreacted benzyl chloroformate. The aqueous layer was then extracted several times with ethyl acetate to give a total of 2.5-3 liters of the extract. The organic layer was then dried ($Na_2SO_4$), filtered and concentrated to give (2) a white solid (98.57 g, 54%), mp 101°-2° C., Anal calcd. for $C_{14}H_{19}NO_6$ C, 56.56, H, Scheme H:
Synthesis of 3-amino 1,5-iminosugars.

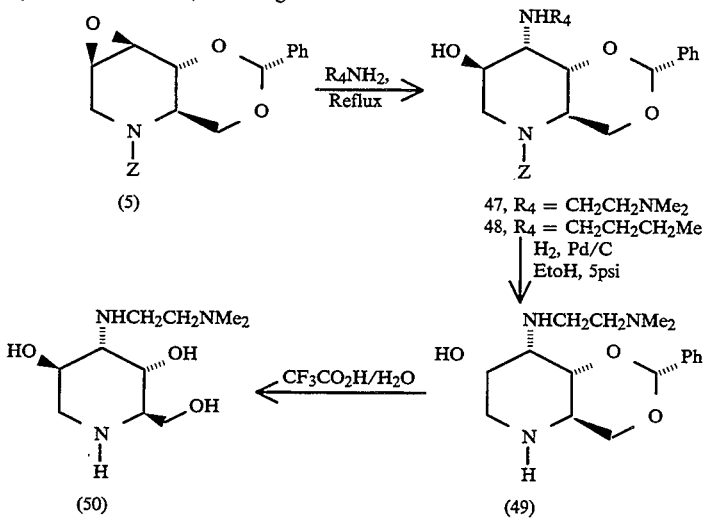

In standard in vitro tests, the novel compounds of the invention were demonstrated to have inhibitory activity against visna virus in a conventional plaque reduction assay. Visna virus, a lentivirus genetically very similar to the AIDS virus, is pathogenic for sheep and goats. See Sonigo et al., *Cell* 42, 369-382 (1985); Haase, *Nature* 322, 130-136 (1986). Inhibition of visna virus replication in vitro as a useful model for human immunodeficiency virus (HIV) and its inhibition by test compounds has been described by Frank et al., *Antimicrobial Agents and Chemotherapy* 31(9), 1369-1374 (1987).

Inhibition of HIV-1 can be shown by tests involving plating of susceptible human host cells which are syncytium-sensitive with and without virus in microculture plates, adding various concentrations of the test compound, incubating the plates for 9 days (during which time infected, non-drug treated control cells are largely or totally destroyed by the virus), and then determining the number of remaining viable cells using a colorimetric endpoint.

6.44, N, 4.71 Found C, 56.33, H, 6.38, N, 4.58., $^1H$ NMR ($CD_3OD$) 7.2-7.4 (m, 5H), 5.15 (s, 2H), 4.23 (br m, 1H), 4.05 (br d., J=8 Hz, 1H), 3.87 (dd, J=6, 4 Hz, 1H), 3.78-3.85 (m, 2H), 3.70-3.78 (m, 2H), 3.45 (br d, J=8 Hz, 1H).

EXAMPLE 2

Preparation of 1,5-dideoxy-1,5-[{(phenylmethoxy)carbonyl}imino]-4,6-O-(R-phenylmethylene)-D-glucitol (3)

A mixture of (2) (98.5 g, 0.33 mmol), benzaldehyde dimethyl acetal (65.5 g, 0.43 mol) and p-toluenesulfonic acid (1 g) in a round bottom flask was dissolved in dimethlformamide (400 ml). The flask was connected to a water aspirator and the reaction was heated to 60°-65° C. for 4 hr. The reaction mixture was cooled to room temperature and poured into stirred ice-water (1200 ml) containing sodium bicarbonate (14 g). The white solid formed was filtered, washed with cold water and dried. Recrystallization using hexane/ethyl acetate gave 3 (96

2 g, 54%) as pure white solid, mp 147°-48° C., Anal calcd. for $C_{21}H_{23}NO_6$ C, 65.44, H, 6.02, N, 3.63 Found C, 65.15, H, 5.93, N, 3.49. IR (KBr) 3420, 1715, 1450, 1425, 1395, 1380, 1365, 1090 cm$^{-1}$; $^1$H NMR (CD$_3$OD) 7.28–7.53 (m, 10H), 5.61 (s, 1H), 5.14 (s, 2H), 4.77 (dd, J=11, 4.6 Hz, 1H), 4.38 (t, J=11 Hz, 1H), 4.16 (dd, J=13.4, 4.2 Hz, 1H), 3.5–3.7 (complex m, 3H), 3.35 (td, J=11, 4.6 Hz), 2.97 (dd, J=13.4, 9.3 Hz, 1H); $^{13}$C NMR (CD$_3$OD) 156.7, 139.4, 138.0, 129.9, 129.7, 129.3, 129.2, 129.1, 127.6, 102.8, 81.9, 77.5, 71.5, 70.6, 68.6, 55.9 and 50.5; MS (CI, NH$_3$, m/e) 386 (M+1).

EXAMPLE 3

Preparation of
1,5-dideoxy-1,5-[{(phenylmethoxy)carbonyl}imino]-4,6O-(R-phenylmethylene)-D-glucitol, 2-( 4-methylbenzenesulfonate) (4)

A mixture of diol 3 (46.3 g, 0.12 mmol) and di-n-butyltin oxide (31.1 g, 0.125 mmol) in methanol (300 ml) was refluxed for 2 hr. The methanol was removed, toluene was added and removed under vaccuum. The residue was dissolved in methylene chloride (300 ml) and triethylamine (20 ml, 0.144 mmol). After cooling to 0° C., p-toluenesulfonyl chloride (25.2 g, 0. 132 mmol) was added. The reaction was stirred at 0° C. for 30 min and then warmed to 20° C. After stirring for 3 hr, the reaction was quenched by adding saturated aqueous sodium bicarbonate. The organic layer was separated and washed with water, 0.5 M KHSO$_4$ and water successively. The organic layer was dried (Na$_2$SO$_4$), filtered and concentrated. The residue was chromatographed (silica gel, hexane/ethyl acetate 7/3) to give pure 4 (50.27 g, 77%) as white solid, mp 115°-17° C., Anal calcd. for $C_{28}H_{29}NO_8S$: C, 62.32, H, 5.42, N, 2.66 Found C, 62.65, H, 5.40, N, 2.62. $^1$H NMR (CDCl$_3$) 7.82 (d, J=7.8 Hz, 2H), 7.35–7.50 (m, 10H), 7.31 (d, J=7.8 Hz, 2H), 5.51 (s, 1H), 5.12 (s, 2H), 4.76 (dd, J=11.4, 4.5 1H), 4.38 (ddd, J=9.3, 7.6, 4.8 Hz, 1H), 3.78 11.4, 9.5 Hz, 1H), 4.31 (dd, J=13.6, 4.8 Hz, 1H), 3.78 (dt, J=2.6, 9.4Hz, 1H), 3.59 (t, J=9.4 Hz, 1H), 3.26 (ddd, J=11.4, 9.4, 4.5 Hz, 1H), 3.04 (dd, J=13.6, 9.3 HZ, 1H) 2.63 (d, J=2.6 Hz, 1H), 2.41 (s, 3H); $^{13}$C NMR (CDCl$_3$) 154.8, 145.2, 137.0, 135.8, 133.2, 129.8, 129.3, 128.7, 128.4, 128.3, 128.1, 126.2, 101.8, 79.9, 78.1, 73.9, 69.2, 67.8, 54.2, 47.1 and 21.7; MS (m/e) 546 (M+Li).

EXAMPLE 4

Preparation of
2,3-anhydro-1,5-dideoxy-1,5-{(phenylmethoxy)carbonyl}imino]-4,6-O-(R-phenylmethylene)-D-mannitol (5)

Sodium hydride (2.79 g, 60% dispersion in mineral oil, 69.66 mol) was placed in a flask under argon and washed three times with dry hexane. The residue was suspended in dry THF (300 ml) and to this a solution of 4 (37.6 g, 69.66 mmol) in THF (100 ml) was added slowly. After stirring for 18 hr, the reaction was quenched by adding water. The organic layer was extacted with ethyl acetate and washed with saturated aqueous sodium bicarbonate and brine. After drying (sodium sulfate) and filteration, the organic layer was concentrated and recrystallized using cyclohexane to give pure 5 (19.2 g, 75%) as white solid, mp 104°-5° C. Anal calcd. for $C_{21}H_{21}NO_5$ C, 68.64, H, 5.77, N, 381 Found C, 68.21, H, 5.84, N, 3.67. $^1$H NMR (CDCl$_3$) 7.53–7.67 (m, 10H), 5.67 (s,1H), 5.16 (s, 2H), 4.76 (broad s, 1H), 4.59 (d, J=15 Hz, 1H), 4.08 (d, J=10 Hz, 1H), 4.02 (dd, J=11.4, 4 Hz, 1H), 3.46 (dd, J=15, 0.9 Hz, 1H), 3.40 (d, J=3 Hz, 1H), 3.25 (d, J=3 Hz, 1H), 3.10 (dr, J=4, 10 Hz, 1H); $^{13}$C NMR (CDCl$_3$) 156.2, 137.8, 136.6, 129.7, 129.1, 128.9, 128.8, 128.5, 126.6, 102.8, 73.0, 70.4, 68.0, 56.0, 54.7, 50.4 and 46.6; MS (CI, NH$_3$, m/e) 368 (M+H).

EXAMPLE 5

Synthesis of
2-azido-1,2,5-trideoxy-1,5-[{(phenylmethoxy)carbonyl)imino]-4,6O-(R-phenylmethylene)-D-glucitol(7) and 3-azido-1,3,5 -trideoxy-1,5-[{(phenylmethoxy) carbonyl}imino]-4,6-O-(R-phenylmethylene)-D-altritol(6)

To a solution of epoxide 5 (4 g, 10.9 mmol) in 2-methoxyethanol (80 ml), sodium azide (3.5 g, 54.5 mmol) and ammonium chloride (2.33 g, 43.6 mmol) were added. The reaction mixture was refluxed for 36 hr. Part of the solvent was removed under reduced pressure. The reaction mixture was diluted with ethyl acetate and washed with 1N HCl, water and brine. The organic layer was dried (MgSO$_4$), filtered and concentrated. The crude mixture was chromatographed (silica gel, hexane/ethyl acetate 8/2) to give pure 7 (1.95 g, 44%) and 6 (1.81 g, 41%). 6. DSC (mp) 253° C.; Anal calcd. for $C_{21}H_{22}N_4O_5$ C, 61.46, H, 5.40, N, 13.65. Found C, 61.23, H, 5.46, N, 13.39 7. Anal calcd. for $C_{21}H_{22}N_4O_5$ C, 61.46, H, 5.40, N, 13.65 Found C, 61.31, H, 5.56, N, 13.26.

EXAMPLE 6

Synthesis of
2-azido-1,2,5-trideoxy-1,5-imino-4,6-O-(R-phenylmethylene)-D-glucitol (8)

The compound 7 (3.3 g, 8.05 mol) was added to previously prepared solution of sodium hydroxide (4 g) in ethanol/water (1/1, 120 ml). After heating the mixture at 70° C. for 20 hr, the reaction was cooled and part of the solvent was removed under reduced pressure. The mixture was neutrallized with 1N HCl and extracted in methylene chloride. The organic layer was washed with water and brine. After drying (MgSO$_4$) and concentration of the filterate, the crude product (3.01 g) was chromatographed (silica gel, ethyl acetae/i-propanol 98/2) to give pure 8 (2.07 g, 93%). Anal calcd. for $C_{13}H_{16}N_4O_3$ C, 56.51, H, 5.84, N, 20.28 Found C, 56.56, H, 5.93, N, 20.15.

EXAMPLE 7

Synthesis of 2-azido-1,5-(butylimino)-1,2,5-trideoxy-4,6-O-(R-phenylmethylene)-D-glucitol (9)

To a solution of 8 (3.1 g, 11.23 mmol) in methanol (120 ml), molecular sieves (4Å, 3.5 g) were added. After stirring for 5 min, butyraldehyde (1.86 ml, 20.8 mol), acetic acid (1.3 ml) and sodium cyanoborohydride (95%, 1.02 g, 15.4 mmol) were added. The reaction was stirred at 22° C. for 18 hr, filtered and the residue washed with more ethyl acetate. The combined organic fractions were concentrated.

The residue was redissolved in ethyl acetate and washed with aqueous potassium carbonate, water and brine. After drying ($MgSO_4$) and concentration, the crude (4.08 g) was chromatographed (silica gel, hexane/ethyl acetate 6/4) to give 9 (3.28 g, 88%) as white solid. DSC (mp) 115° C. (dec.); Anal calcd. for $C_{17}H_{24}N_4O_3$ C, 61.43, H, 7.28, N, 16.85 Found C, 61.40, H, 7.34, N, 16.84.

EXAMPLE 8

Synthesis of 2-azido-1,5-{(2-ethylbutyl)imino}-1,2,5-trideoxy-4,6-O-(R-phenylmethylene)-D-glucitol (10)

To a solution of 8 (1.07 g, 3.87 mmol) in methanol (35 ml), molecular sieves (4Å, 2.1 g) were added. After stirring for 5 min, 2-ethylbutyraldehyde (1.04 ml, 7.74 mol), acetic acid (0.35 ml) and sodium cyanoborohydride (95%, 390 mg, 5.8 mmol) were added. The reaction was stirred at 22° C. for 20 hr, filtered and the residue washed with more ethyl acetate. The combined organic fractions were concentrated. The residue was redissolved in ethyl acetate and washed with aqueous potassium carbonate, water and brine. After drying ($MgSO_4$) and concentration, the crude (1.47 g) was chromatographed (silica gel, hexane/ethyl acetate 8/2) to give pure 10 (650 mg, 47%). Anal calcd. for $C_{19}H_{28}N_4O_3$ C, 62.68, 7.86, N, 15.39 Found C, 62.72, H, 7.94, N, 15.16.

EXAMPLE 9

Synthesis of 2-azido-1,5-{(4,4,4-trifluorobutyl)imino}-1,2,5-trideoxy-4,6-0- (R-phenylmethylene)-D-glucitol (11)

To a solution of 8 (500 rag, 1.81 mmol) in dimethylformamide (10 ml), 1-bromo-4,4,4-trifluorobutane (375 mg, 1.96 mmol) and potassium carbonate (150 mg, 1.08 mmol) were added. The reaction was immersed in an oil-bath at 60° C. and stirred for 60 hr. More 1-bromo-4,4,4-trifluorobutane (375 mg, 1.96 mmol) was added and the reaction was heated at 60° C. for 24 hr. The solvent was removed under reduced pressure and the reaction mixture was neutralized with 1N HCl. The mixture was extracted in methylene chloride and the extract was washed with aqueous potassium carbonate and brine. After drying ($MgSO_4$) and concentration, the crude (610 mg) was chromatographed (silica gel, hexane/ethyl acetate 6/4) to give pure 11 (510 mg, 73%) as thick liquid. $^1H$ NMR ($CDCl_3$) 7.49 (m, 2H), 7.39 (m, 3H), 5.49 (s, 1H), 4.34 (dd, J=11, 4 Hz, 1H), 3.63 (dd, J=11, 10 Hz, 1H), 3.45–3.60 (complex band, 2H), 3.48 (t, J=9 Hz, 1H), 3.10 (d, J=2 Hz, 1H), 2.97 (dd, J=12, 5 Hz, 1H), 2.55 (dt, J=13, 5 Hz, 1H), 2.36 (td, J=10, 4 Hz, 1H), 2.30 (dt, J=13, 7 Hz, 1H), 1.90–2.22 (complex band, 3H), 1.68 (d, J=7.5 Hz, 1H).

EXAMPLE 10

Synthesis of 2-azido-1,2,5-trideoxy-1,5-imino-D-glucitol (12)

A solution of 8 (1 g, 3.61 mmol) in trifluoroacetic acid/water (4/1, 15 ml) was stirred at 22° C. for 18 hr. The solvent was removed under reduced pressure and the residue as thick yellow liquid was passed through an ion-exchange column [Amberlite, IRA-400 (OH)] prewashed with distilled water until neutral. The basic fractions, as also followed by TLC (silica gel, ethyl acetate/methanol/ammonium hydroxide 50/50/2.5), were pooled and concentrated. The water in the fractions was azeotropically removed with toluene and 12 (394 mg, 74%) was isolated as a white solid after crystallization from methanol/hexane, mp 142° C. (dec). Anal calcd. for $C_6H_{12}N_4O_3 \cdot .25H_2O$ C, 39.86, H, 6.64, N, 27.75 Found C, 39.91, H, 6.79, N, 27.59.

EXAMPLE 11

Synthesis of 2-azido-1,5-(butylimino)-1,2,5-trideoxy-D-glucitol (13)

A solution of 9 (650 mg, 1.96 mmol) in trifluoroacetic acid/water (4/1, 12 ml) was stirred at 22° C. for 8 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/water/ammonium hydroxide 70/25/5/2), were pooled and concentrated. The water in the fractions was azeotropically removed with toluene to give 13 (330 mg) which was rechromatographed (silica gel, ethyl acetate/i-propanol/water/ammonium hydroxide 70/25/5/2) to give pure 13 (260 mg, 61%) as thick liquid. Anal calcd. for $C_{10}H_{20}N_4O_3 \cdot 2H_2O$ C, 48.45, H, 8.29, N, 22.60 Found C, 48.49, H, 8.31, N, 22.41.

EXAMPLE 12

Synthesis of 2-azido-1,5-{(2-ethylbutyl)imino}-1,2,5-trideoxy-D-glucitol (14)

A solution of 10 (250 mg, 0.69 mmol) in trifluoroacetic acid/water (4/1, 7 ml) was stirred at 22° C. for 18 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/water/ammonium hydroxide 70/25/5/2), were pooled and concentrated. The water in the fractions was azeotropically removed with toluene to give 14 (151 mg) which was rechromatographed (silica gel, ethyl acetate/i-propanol/water/ammonium hydroxide 70/25/5/2) to give pure 14 (52 mg, 27%). DSC (mp) 127° C. (dec). Anal calcd. for $C_{12}H_{24}N_4O_3$ C, 52.92, H, 8.88, N, 20.57 Found C, 52.67, H, 8.91, N, 20.48.

EXAMPLE 13

Synthesis of 2-azido-1,5-{(4,4,4-trifluorobutyl)imino}-1,2,5-trideoxy-D-glucitol(15)

A solution of 11 (500 mg, 1.29 mmol) in trifluoroacetic acid/water (4/1, 25 ml) was stirred at 22° C. for 24 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/-water/ammonium hydroxide 70/25/5/2), were pooled and concentrated. The water in the fractions was azeotropically removed with toluene to give crude 15 (320 mg) which was rechromatographed (silica gel, ethyl acetate/i-propanol/water/ammonium hydroxide 70/25/5/2) to give pure 15 (272 mg, 70%) as white solid. DSC (mp) 107° C. (dec). Anal calcd. for $C_{10}H_{17}N_4O_3F_3$ C, 40.27, H, 5.75, N, 18.78 Found C, 40.12, H, 5.71, N, 18.60.

EXAMPLE 14

Synthesis of
2-amino-1,5-(butylimino)-1,2,5-trideoxy-4,6-O-(R-phenylmethylene)-D-glucitol (17)

To a solution of 9 (700 mg, 2.11 mmol) in methanol (70 ml) in a Parr hydrogenation flask, 10% Pd on C (70 mg) was added. The system was sealed, purged with nitrogen (5 times) and hydrogen (5 times) and then pressurized to 5 psi hydrogen. After running the reaction on a shaker for 3.5 hr, the system was vented, purged with nitrogen and filtered. The filtrate was concentrated and the crude (630 mg) was chromatographed (silica gel, methylene chloride/methanol/ammonium hydroxide 90/10/1) to give pure 17 (600 mg, 93%). DSC (mp) 125° C. Anal calcd. for $C_{17}H_{26}N_2O_3$ C, 66.64, H, 8.55, N, 9.14 Found C, 66.14, H, 8.56, N, 9.08.

EXAMPLE 15

Synthesis of
2-amino-1,5-{(2-ethylbutyl)imino}-1,2,5-trideoxy-4,6-O-(R-phenylmethylene)-D-glucitol (18)

To a solution of 10 (350 mg, 0.97 mmol) in methanol (50 ml) in a Parr hydrogenation flask, 10% Pd on C (35 mg) was added. The system was sealed, purged with nitrogen (5 times) and hydrogen (5 times) and then pressurized to 5 psi hydrogen. After running the reaction on a shaker for 3 hr, the system was vented, purged with nitrogen and filtered. The filtrate was concentrated and the crude (320 mg) was chromatographed (silica gel, methylene chloride/methanol/ammonium hydroxide 90/10/1) to give pure 18 (240 mg, 78%). Anal calcd. for $C_{19}H_{30}N_2O_3$ C, 68.23, H, 9.04, N, 8.38 Found C, 68.87, H, 9.01, N, 7.48.

EXAMPLE 16

Synthesis of
2-amino-1,5-{(4,4,4-trifluorobutyl)imino}-1,2,5-trideoxy-4,6-O-(R-phenylmethylene)-D-glucitol (19)

To a solution of 11 (1.4 g, 3.63 mmol) in methanol (25 ml) in a Parr hydrogenation flask, 10% Pd on C (140 mg) was added. The system was sealed, purged with nitrogen (5 times) and hydrogen (5 times) and then pressurized to 5 psi hydrogen. After running the reaction on a shaker for 21 hr, the system was vented, purged with nitrogen and filtered. The filtrate was concentrated and the crude (1.3 g) was chromatographed (silica gel, methylene chloride/methanol/ammonium hydroxide 90/10/1) to give pure 19 (1.15 g, 88%). Anal calcd. for $C_{17}H_{23}N_2O_3F_3$·0.4H$_2$O C, 55.55, H, 6.53, N, 7.62 Found C, 55.55, H, 6.36, N, 7.59.

EXAMPLE 17

Synthesis of
2-amino-1,2,5-trideoxy-1,5-imino-D-glucitol (20)

To a solution of 12 (465 mg, 3.14 mmol) in methanol (50 ml) in a Parr hydrogenation flask, 10% Pd on C (50 mg) was added. The system was sealed, purged with nitrogen (5 times) and hydrogen (5 times) and then pressurized to 5 psi hydrogen. After running the reaction on a shaker for 3.5 hr, the system was vented, purged with nitrogen and filtered. The filtrate was concentrated to give pure 20 (365 mg, 91%). DSC (mp) 184° C.. Anal calcd. for $C_6H_{14}N_2O_3$·0.25H$_2$O C, 43.23, H, 8.77, N, 16.81 Found C, 43.42, H, 8.43, =N, 16.47.

EXAMPLE 18

Synthesis of
2-amino-1,5-(butylimino)-1,2,5-trideoxy-D-glucitol(21)

A solution of 17 (580 mg, 1.89 mmol) in trifluoroacetic acid/water (4/1, 15 ml) was stirred at 22° C. for 24 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/methanol-/ammonium hydroxide 50/50/2.5), were pooled and concentrated. The water in the fractions was azeotropically removed with toluene to give crude 21 (410 mg) which was rechromatographed (silica gel, ethyl acetate/methanol/ammonium hydroxide 50/50/2.5) to give pure 21 (302 mg, 73%). DSC (mp) 108° C. Anal calcd. for $C_{10}H_{22}N_2O_3$·0.3H$_2$O C, 53.69, H, 10.18, N, 12.52 Found C, 53.63, H, 10.02, N, 12.34.

EXAMPLE 19

Synthesis of
2-amino-1,5-{(2-ethylbutyl)imino}-1,2,5-trideoxy-D-glucitol (22)

A solution of 18 (140 mg, 0.42 mmol) in trifluoroacetic acid/water (4/1, 10 ml) was stirred at 22° C. for 8 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/ammonium hydroxide 50/50/2.5), were pooled and concentrated. The water in the fractions was azeotropically removed with toluene to give crude 22 (120 mg) which was rechromatographed (silica gel, ethyl acetate/i-propanol/ammonium hydroxide 50/50/2.5) to give pure 22 (72 mg, 70%). DSC (mp) 130° C. Anal calcd. for $C_{12}H_{26}N_2O_3$·0.75H$_2$O C, 55.46, H, 10.67, N, 10.78 Found C, 55.33, H, 10.05, N, 10.54.

EXAMPLE 20

Synthesis of
2-amino-1,5-{(4,4,4-trifluorobutyl)imino}-1,2,5-trideoxy-D-glucitol (23)

A solution of 19 (400 mg, 1.1 mmol) in trifluoroacetic acid/water (4/1, 10 ml) was stirred at 22° C. for 8 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/ammonium hydroxide 50/50/2.5), were pooled and concentrated. The water in the fractions was azeotropically removed with toluene to give crude 23 (280 mg) which was rechromatographed (silica gel, ethyl acetate/i-propanol/ammonium hydroxide 50/50/2.5) to give pure 23 (265 mg, 87%). Anal calcd. for $C_{10}H_{19}N_2O_3F_3$ 0.3H$_2$O C, 43.26, H, 7.11, N, 10.09 Found C, 43.23, H, 6.86, N, 9.59.

EXAMPLE 21

Synthesis of 1,5-(butylimino)-1,2,5-trideoxy-2-(dimethylamino)-4,6-O-(R-phenylmethylene)-D-glucitol (24) and 1,5-(butylimino)-1,2,5-trideoxy-2-(methylamino)-4,6-O-(R-phenylmethylene)-D-glucitol (25)

To a solution of 17 (792 mg, 2.59 mmol) in methanol (75 ml) in a Parr hydrogenation flask, 4% Pd on C (100 mg) and formaldehyde (0.23 ml) were added. The system was sealed, purged with nitrogen (5 times) and hydrogen (5 times) and then pressurized to 5 psi hydrogen. After running the reaction on a shaker for 21 hr, the system was vented, purged with nitrogen and filtered. The filtrate was concentrated and the crude (560 mg) was chromatographed (silica gel, methylene chloride/methanol/ammonium hydroxide 90/10/1) to give 24 (310 rag, 36%) and 25 (372 rag, 45%).

24. $^1$H NMR (CDCl$_3$) 7.52 (m, 2H), 7.34 (m, 3H), 5.52 (s, 1H), 4.37 (dd, J=11, 5 Hz, 1H), 3.83 ( brs, 1H), 3.65 (dd, J=11, 10 Hz, 1H), 3.60 (t, J=9 Hz, 1H), 3.54 (t, J=9 Hz, 1H), 2.93 (dd, J=11, 4 Hz, 1H), 2.63 (ddd, J=11, 9, 4 Hz, 1H), 2.53 (dr, J=13, 8 Hz, 1H), 2.35 (s, 6H), 2.22–2.37 (complex band, 2H), 2.14 (t, J=11 Hz, 1H), 1.42 (m, 2H), 1.27 (m, 2H), 0.92 (t, J=7 Hz, 3H).

25. $^1$H NMR (CDCl$_3$) 7.49 (m, 2H), 7.34 (m, 3H), 5.49 (s, 1H), 4.36 (dd, J=11, 4 Hz, 1H), 3.65 (dd, J=11, 10 Hz, 1H), 3.48 (t, J=9 Hz, 1H), 3.36 (dd, J=10, 9 Hz, 1H), 3.25 (broad s, 1H), 3.05 (dd, J=11, 5 Hz, 1H), 2.57 (td, J=10, 5 Hz, 1H), 2.51 (dt, J=13, 8 Hz, 1H), 2.39 (ddd, J=10, 9, 4 Hz, 1H), 2.37 (s, 3H), 2.30 (ddd, J=13, 8, 6 Hz, 1H), 2.00 (t, J=11 Hz, 1H), 1.42 (m, 2H), 1.26 (m, 2H), 0.92 (t, J=7 Hz, 3H).

EXAMPLE 22

1,5 (butylimino)-1,2,5-trideoxy-2-{(1-oxobutyl)amino}-4,6-O-(R-phenylmethylene)-D-glucitol, 3-butanoate (26)

To a solution of 17 (650 mg 2.12 mmol) in pyridine (8 ml), butyric anhydride (2 ml) was added and the reaction mixture was stirred at room temperature. After stirring for 18 hr, the reaction mixture was poured over ice and extracted with methylene chloride. The organic layer was washed with water and brine. After drying over MgSO$_4$, the extract was filtered and the solvent removed under reduced pressure. The crude product 26 (1.01 g) was used in the next step without further purification. $^1$H NMR (CDCl$_3$) 7.45 (m, 2H), 7.36 (m, 3H), 5.86 (d, J=7.5 Hz, 1H), 5.53 (s, 1H), 4.92 (t, J=10 Hz, 1H), 4.43 (dd, J=11, 5 Hz, 1H), 4.16 (tdd, J=10, 7.5, 5 Hz, 1H), 3.74 (t, J=10 Hz, 1H), 3.73 (dd, J=11, 10 Hz, 1H), 3.25 (dd, J=12, 5 Hz, 1H), 2.55 (dt, J=13, 8 Hz, 1H), 2.46 (td, J=10, 5 Hz, 1H), 2.35 (dt, J=15, 7.5 Hz, 1H), 2.29 (dr, J=15, 7.5 Hz, 1H), 2.27 (dt, J=13, 7 Hz, 1H), 2.10 (t, J=7.5 Hz, 2H), 2.06 (dd, J=12, 10 Hz, 1H), 1.62 (m, 4H), 1.41 (m, 2H), 1.27 (m, 2H), 0.93 (t, J=7.5 Hz, 1H), 0.90 (t, J=7.5 Hz, 1H).

EXAMPLE 23

1,5-(butylimino)-1,2,5-trideoxy-2-{(1-oxobutyl)amino}-4,6-O-(R-phenylmethylene)-D-glucitol (27)

To a solution of 26 (900 rag, 2.01 mmol) in methanol (50 ml), saturated aqueous potassium carbonate (30 ml) was added and the mixture was stirred at room temperature for 4 hr. After neutralizing with conc. HCl to pH 7, methanol was removed under reduced pressure and the reaction mixture was extracted with ethyl acetate. The organic layer was washed with water and brine, dried (MgSO$_4$) and filtered. The concentration of the extract gave 27 (720 mg, 90%). mp 172° C. (dec), Anal calcd. for $C_{21}H_{32}N_2O_4$, C, 66.99, H, 8.57, N, 7.44 Found C, 66.82, H, 8.68, N, 7.36.

EXAMPLE 24

Synthesis of 1,5-(butylimino)-1,2,5-trideoxy-2-(dimethylamino)-D-glucitol (28)

A solution of 24 (580 mg, 1.74 mmol) in trifluoroacetic acid/water (4/1, 10 ml) was stirred at 22° C. for 24 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/ammonium hydroxide 50/50/2.5), were pooled and concentrated. The water in the fractions was azeotropically removed with toluene to give crude 28 (300 mg) which was rechromatographed (silica gel, ethyl acetate-/i-propanol/ammonium hydroxide 50/50/2.5) to give pure 28 (260 mg, 61%). DSC (mp) 111° C., Anal calcd. for $C_{12}H_{26}N_2O_3$ 0.2 H$_2$O, C, 57.66, H, 10.65, N, 11.21 Found C, 57.88, H, 10.63, N, 11.23.

EXAMPLE 25

Synthesis of 1,5-(butylimino)-1,2,5-trideoxy-2-(methylamino)-D-glucitol (29)

A solution of 25 (610 mg, 1.91 mmol) in trifluoroacetic acid/water (4/1, 10 ml) was stirred at 22° C. for 24 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/ammonium hydroxide 50/50/2.5), were pooled and concentrated. The water in the fractions was azeotropically removed with toluene to give crude 29 (480 mg) which was rechromatographed (silica gel, ethyl acetate-/i-propanol/ammonium hydroxide 50/50/2.5) to give pure 29 (310 mg, 70%). Anal calcd. for $C_{11}H_{24}N_2O_3$ 0.4 H$_2$O, C, 55.16, H, 10.44, N, 11.70 Found C, 55.24, H, 10.57, N, 11.74.

EXAMPLE 26

1,5-(butylimino)-1,2,5-trideoxy-2-{(1-oxobutyl)amino}-D-glucitol (30)

A solution of 27 (250 mg, 0.66 mmol) in trifluoroacetic acid/water (4/1, 10 ml) was stirred at 22° C. for 24 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/i-propanol/- water/ammonium hydroxide 70/25/5/2), were pooled and concentrated. The water in the fractions was azeotropically removed with toluene to give crude 30 (180 mg) which was rechromatographed (silica gel, ethyl acetate/i-propanol/water/ammonium hydroxide 70/25/5/2) to give pure 30 (165 mg, 86%). DSC (mp) 203° C., Anal calcd. for $C_{14}H_{28}N_2O_4$ 0.5 $H_2O$, C, 56.54, H, 9.83, N, 9.42 Found C, 56.32, H, 9.50, N, 9.26.

EXAMPLE 27

1,5-(butylimino)-1,2,5-trideoxy-2-{(1-oxobutyl)amino}-D-glucitol, tributanoate (31)

To a solution of 30 (100 mg 0.34 mmol) in pyridine (8 ml), butyric anhydride (2 ml) was added and the reaction mixture was stirred at room temperature. After stirring for 40 hr, the reaction mixture was poured over ice and extracted with methylene chloride. The organic layer was washed with water and brine. After drying over $MgSO_4$, the extract was filtered and the solvent removed under reduced pressure. The crude product (280 mg) was chromatographed (silica gel, hexane/ethyl acetate 6/4) to give pure 31 (98 mg, 57%). DSC (mp) 84° C. (dec), Anal calcd. for $C_{26}H_{46}N_2O_7$, C, 62.63, H, 9.30, N, 5.62 Found C, 62.17, H, 9.30, N, 5.32.

EXAMPLE 28

Synthesis of phenylmethyl 8β-azidohexahydro-7-oxo-2R-2α-phenyl-5H-4aα, 8aβ-1,3-dioxino[5,4-b]pyridine-5-carboxylate (32)

To a cold solution of dimethyl sulfoxide (5.6 ml, 78 mmol) in methylene chloride (50 ml) at −70° C., trifluoroacetic anhydride (8.32 ml, 59 mmol) in methylene chloride (50 ml) was added over 20 min. After stirring for 15 min, a solution of 6 (16 g, 39 mmol) in methylene chloride (150 ml) was added over 30 min. at −70° C. The temperature of reaction mixture was allowed to rise to −30° C. over 4 hr and then the reaction was stirred at −30° C. for 1 hr. After recooling to −70° C., triethylamine (15 ml, 107 mmol) was added and the reaction was warmed to 22° C. in about an 1 hr and stirred at 22° C. for about 8 hr. The reaction was diluted with methylene chloride and washed with water and brine. After drying (MgSO₄), filteration and concentration, the crude (17.8 g) was chromatographed (silica gel, hexane/ethyl acetate 1/1) to give pure 32 (13.9 g, 86%). $^1$H NMR (CDCl₃) 7.30-7.49 (complex band, 10H), 5.71 (s, 1H), 5.13 (s, 2H), 4.85 (d, J=11 Hz, 1H), 4.61 (dd, J=11, 4 Hz, 1H), 4.33 (dd, J=11, 10 Hz, 1H), 4.30 (d, J=18 Hz, 1H), 4.20 (d, J=18 Hz, 1H), 4.11 (dd, J=11, 10, 1H), 3.85 (dt, J=10, 4Hz, 1H).

EXAMPLE 29

3-azido-1,3,5-trideoxy-1,5-[{(phenylmethoxy)carbonyl-}imino]-4,6-O-(R-phenylmethylene)-D-glucitol (33) and 3-azido-1,3,5-trideoxy-1,5-[{(phenylmethoxy)carbonyl-}imino]-4,6-O-(R-phenylmethylene)-D-mannitol (34)

To a cold solution of 32 (2.5 g,; 6.12 mmol) in THF (100 ml) at −78° C., diisobutylaluminum hydride (9.25 ml, 1 M solution in toluene, 9.25 mmol) was added over 10 min. After stirring at −78° C. for 4 hr, methanol (2.5 ml) was added. The reaction was stirred for 10 min, the cold bath was removed and the reaction allowed to rise to 22° C. and stirred for 30 min. After quenching with 0.5 N HCl (10 ml), the reaction was diluted with ethyl acetate and washed with water and brine. The organic extract was dried (MgSO₄), filtered and concentrated to give crude mixture (2.23 g) as thick orange liquid. Chromatographic purification (silica gel, hexane/ethyl acetate 1/1) gave 33 (1.57 g, 63%) and 34 (231 mg, 9%). 33. Anal calcd. for $C_{21}H_{22}N_4O_5$, C, 61.46, H, 5.40, N, 13.65 Found C, 61.62, H, 5.53, N, 12.48. 34. Anal calcd. for $C_{21}H_{22}N_4O_5$, C, 61.46, H, 5.40, N, 13.65 Found C, 61.37, H, 5.43, N, 13.39.

EXAMPLE 30

3-azido-1,3,5-trideoxy-1,5-imino-4,6-O-(R-phenylmethylene)-D-glucitol (35)

The compound 33 (1.8 g, 4.39 mol) was added to previously prepared solution of sodium hydroxide (2 g) in ethanol/water (1/1, 60 ml). After heating the mixture at 75°-80° C. for 20 hr, the reaction was cooled and part of the solvent was removed under reduced pressure. The mixture was neutrallized with 1N HCl and extracted in methylene chloride. The organic layer was washed with water and brine. After drying (MgSO₄) and concentration of filterate, the crude product (3.01 g) was chromatographed (silica gel, methylene chloride/methanol/ammonium hydroxide 90/10/1) to give pure 35 (1.1 g, 91%). DSC (mp) 192° C., Anal calcd. for $C_{13}H_{16}N_4O_3$, C, 56.51, H, 5.84, N, 20.28 Found C, 56.26, H, 5.90, N, 20.08.

EXAMPLE 31

3-amino-1,3,5-trideoxy-1,5-imino-4,6-O-(R-phenylmethylene)-D-glucitol(36)

To a solution of 35 (700 mg, 2.54 mmol) in methanol (50 ml) in a Parr hydrogenation flask, 4% Pd on C (150 mg) was added. The system was sealed, purged with nitrogen (5 times) and hydrogen (5 times) and then pressurized to 5 psi hydrogen. After running the reaction on a shaker for 10 hr, the system was vented, purged with nitrogen and filtered. The filtrate was concentrated and the crude (700 mg) was chromatographed (silica gel, methylene chloride/methanol/ammonium hydroxide 90/10/1) to give pure 36 (590 mg, 93%). Anal calcd. for $C_{13}H_{18}N_2O_3$ 0.25$H_2O$, C, 61.28, H, 7.32, N, 10.99 Found C, 61.27, H, 7.29, N, 10.72.

EXAMPLE 32

3-amino-1,3,5-trideoxy-1,5-imino-D-glucitol )37)

A solution of 36 (480 mg, 1.92 mmol) in trifluoroacetic acid/water (4/1, 8 ml) was stirred at 22° C. for 24 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/methanol/ammonium hydroxide 25/75/3), were pooled and concentrated. The water in the fractions was azeotropically removed with toluene to give crude 37 which was rechromatographed (silica gel, ethyl acetate/methanol/ammonium hydroxide 25/75/3) to give pure 37 (135 mg, 32%). DSC (mp) 191° C., Anal calcd. for $C_6H_{14}N_2O_3$ 0.25$H_2O$, C, 43.23, H, 8.77, N, 16.81 Found C, 43.66, H, 8.61, N, 16.19.

EXAMPLE 33

Synthesis of
2-azido-1,2,5-trideoxy-1,5-[{(phenylmethoxy)carbonyl}imino]-4,6-O-(R-phenylmethylene)-D-glucitol, methanesulfonate (38)

To a solution of 7 (3.8 g, 9.27 mmol) in pyridine (40 ml), methanesulfonyl chloride (860 μl, 11.11 mmol) was injected over 10 min. After stirring at 22° C. for 20 hr, the reaction contents were poured over ice and extracted in ethyl acetate (2×700). The combined organic extracts were washed with saturated aqueous potassium carbonate, water and brine. After drying (MgSO$_4$), filteration and concentration, the crude (6.45 g) was chromatographed (silica gel, hexane/ethyl acetate 6/4) to give pure 38(4.3 g, 95%) as white solid. DSC (mp) 222° C., Anal calcd. for $C_{22}H_{24}N_4O_7S$ 1H20, C, 52.17, H, 5.17, N, 11.06 Found C, 52.29, H, 4.81, N, 10.87.

EXAMPLE 34

Synthesis of
2-azido-1,2,5-trideoxy-1,5-[{(phenylmethoxy)carbonyl}imino]-4,6-O-(R-phenylmethylene)-D-allitol, acetate (39)

A mixture of 38 (2.3 g, 4.7 mmol), cesium acetate (9 g, 47 mmol), 18-crown-6 (1.16 g, 4.7 mmol) in toluene (50 ml) was refluxed-for 72 hr. The reaction was cooled, filtered and the residue washed with more toluene. The combined organic fractions were concentrated and the crude (3.36 g) was chromatographed (silica gel, hexane/ethyl acetate 7/3) to give pure 39 (1.1 g, 52%) as white solid in addition to the starting material 38 (0.31 g, 14%). 39. $^1$H NMR (CDCl$_3$) 7.31–7.45 (complex band, 10H), 5.74 (td, J=3, I Hz, 1H), 5.56 (s, 1H), 5.15 (d, J=12 Hz, 1H). 5.11 (d, J=12 Hz, 1H), 4.84 (dd, J=12, 5 Hz, 1H), 4.48 (dd, J=12, 10 Hz, 1H), 4.32 (ddd, J=13, 5, 1 Hz, 1H), 3.79 (dd, J=10, 3 Hz, 1H), 3.61 (td, J=10, 5 Hz, 1H), 3.52 (ddd, J=11, 5, 3 Hz, 1H), 3.16 (dd, J=13, 11 Hz, 1H), 2.17 (s, 3H).

EXAMPLE 35

Synthesis of
2-azido-1,2,5-trideoxy-1,5-[{(phenylmethoxy)carbonyl}imino] -4,6-O-(R-phenylmethylene)-D-allitol (40A) and
2-azido-1,2,5-trideoxy-1,5-{(methoxycarbonyl)imino}-4,6-O-(R-phenylmethylene)-D-allitol (40B)

A mixture of 39 (970 mg, 2.15 mmol) and sodium methoxide (400 mg, 7.4 mmol) in methanol (50 ml) was refluxed for 18 hr. The reaction was cooled, neutrallized with 1N HCl and the solvent removed under reduced pressure. The residue was suspended in ethyl acetate and washed with saturated aqueous potassium carbonate, water and brine. The combined organic extracts were concentrated and the crude (1.02 g) chromatographed (silica gel, hexane/ethyl acetate 7/3) to give 40A (550 mg, 57%) and 40B (270 mg, 35%).

40A. $^1$H NMR (CDCl$_3$) 7.45 (m, 2H), 7.34 (m, 8H), 5.55 (s, 1H), 5.10 (d, J=12 Hz, 1H). 5.07 (d, J=12 Hz, 1H), 4.79 (dd, J=12, 5 Hz, 1H), 4.45 (dd, J=12, 10 Hz, 1H), 4.22 (broad s, 1H), 4.17 (m, 1H), 3.62 (td, J=10, 5 Hz, 1H), 3.54 (dr, J=10, 2 Hz, 1H), 3.24 (m, 1H), 3.21 (m, 1H), 2.87 (s, 1H).

40B. $^1$H NMR (CDCl$_3$) 7.47 (m, 2H), 7.37 (m, 3H), 5.59 (s, 1H), 4.81 (dd, J=12, 4 Hz, 1H), 4.48 (dd, J=12, 9 Hz, 1H), 4.27 (broad s, 1H), 4.12 (dd, J=12, 2 Hz, 1H), 3.67 (s, 3H), 3.65 (m, 1H), 3.60 (m, 1H), 3.30 (m, 1H), 3.23 (m, 1H), 2.82 (broad s, 1H).

EXAMPLE 36

Synthesis of
2-azido-1,2,5-trideoxy-1,5-[{(phenylmethoxy)carbonyl}imino]-4,6-O-(R-phenylmethylene)-D-allitol, methanesulfonate (41A)

To a solution of 40A (550 mg, 1.34 mmol) in pyridine (10 ml), methanesulfonyl chloride (140 μl, 1.74 mmol) was injected over 10 min. After stirring at 22° C. for 60 hr, the reaction contents were poured over ice and extracted in ethyl acetate. The combined organic extracts were washed with saturated aqueous potassium carbonate, water and brine. After drying (MgSO$_4$), filteration and concentration, the product obtained 41A (603 mg, 92%) was used in the next step without further purification. $^1$H NMR (CDCl$_3$) 7.44 (m, 2H), 7.35 (m, 8H), 5.58 (s, 1H), 5.15 (broad t, J=2.5 Hz, 1H), 5.11 (s, 2H), 4.87 (dd, J=12, 5 Hz, 1H), 4.45 (dd, J=12, 10 Hz, 1H), 4.31 (dd, J=13, 5 Hz, 1H), 3.80 (dd, J=10, 2 Hz, 1H), 3.60 (ddd, J=12, 5, 3 Hz, 1H), 3.56 (td, J= 10, 5 Hz, 1H), 3.10 (dd, J=13, 12 Hz, 1H), 2.92 (s, 3H).

EXAMPLE 37

Synthesis of
2-azido-1,2,5-trideoxy-1,5-{(methoxycarbonyl)imino}-4,6-O-(R-phenylmethylene)-D-allitol, methanesulfonate (41B)

To a solution of 40B (217 mg, 0.65 mmol) in pyridine (5 ml), methanesulfonyl chloride (65 μl, 0.84 mmol) was injected over 10 min. After stirring at 22° C. for 30 hr, the reaction contents were poured over ice and extracted in ethyl acetate. The combined organic extracts were washed with saturated aqueous potassium carbonate, water and brine. After drying (MgSO$_4$), filteration and concentration, the product obtained 41B (320 mg, 92%) was used in the next step without further purification. $^1$H NMR (CDCl$_3$) 7.46 (m, 2H), 7.35 (m, 3H), 5.61 (s, 1H), 5.18 (broad t, J=2.5 Hz, 1H), 4.88 (dd, J=12, 5 Hz, 1H), 4.48 (dd, J=12, 10 Hz, 1H), 4.28 (dd, J=13, 5 Hz, 1H), 3.83 (dd, J=10, 2 Hz, 1H), 3.70 (s, 3H), 3.66 (ddd, J=12, 5, 3 Hz, 1H), 3.58 (td, J=10, 5 Hz, 1H), 3.12 (dd, J=13, 12 Hz, 1H), 2.95 (s, 3H).

EXAMPLE 38

Synthesis of
2,3-diazido-1,2,3,5-tetradeoxy-1,5-{(methoxycarbonyl)imino}-4,6-O-(R-phenylmethylene)-D-glucitol(42B)

To a solution of 41B (320 mg, 0.77 mmol) in dimethylformamide (10 ml), sodium azide (252 mg, 3.88 mmol) was added. The reaction mixture was heated at 100–10° C. for 30 hr. Part of the solvent was removed under reduced pressure. The reaction mixture was diluted with ethyl acetate and washed with aqueous potassium carbonate, water and brine. The organic layer was dried (MgSO$_4$), filtered and concentrated. The crude 42B (190 mg, 69%) was used in the next step without further purification. $^1$H NMR (CDCl$_3$) 7.50 (m, 2H), 7.37 (m, 3H), 5.62 (s, 1H), 4.79 (dd, J=12, 5 Hz, 1H), 4.45 (dd, J=12, 10 Hz, 1H), 4.28 (dd, J=14, 5 Hz, 1H), 3.68 (s, 3H), 3.67 (t, J=10 Hz, 1H), 3.50 (t, J=10 Hz, 1H), 3.30 (ddd, J=11, 10, 5 Hz, 1H), 3.20 (td, J=10, 5 Hz, 1H), 2.64 (dd, J=14, 11 Hz, 1H).

EXAMPLE 39

Synthesis of
2,3-diazido-1,2,3,5-tetradeoxy-1,5-[{(phenylmethoxy)-carbonyl}imino]-4,6-O-(R-phenylmethylene)-D-glucitol(42A)

To a solution of 41A (600 mg, 1.23 mmol) in dimethylformamide (10 ml), sodium azide (400 mg, 6.15 mmol) was added. The reaction mixture was heated at 100-10° C. for 72 hr. Part of the solvent was removed under reduced pressure. The reaction mixture was diluted with ethyl acetate and washed with aqueous potassium carbonate, water and brine. The organic layer was dried (MgSO$_4$), filtered and concentrated. The crude mixture (760 mg) consisting of 42A and 43 was hydrolyzed to 43 without purification.

EXAMPLE 40

Synthesis of
2,3-diazido-1,2,3,5-tetradeoxy-1,5-imino-4,6-O-(R-phenylmethylene)-D-glucitol (43)

The mixture of 42A, 42B & 43 (920 mg) obtained in the above steps was added to previously prepared solution of sodium hydroxide (2 g) in ethanol/water (1/1, 60 ml). After refluxing the mixture for 20 hr, the reaction was cooled and part of the solvent was removed under reduced pressure. The mixture was neutralllized with 1N HCl and extracted in ethyl acetate. The organic layer was washed with water and brine. After drying (MgSO$_4$) and concentration of filterate, the crude product (280 mg) was chromatographed (silica gel, methylene chloride/ethanol 98/2) to give pure 43. (360 mg, 68% in two steps). $^1$H NMR (CDCl$_3$) 7.56 (m, 2H), 7.43 (m, 3H), 5.61 (s, 1H), 4.23 (dd, J=11, 5 Hz, 1H), 3.58 (dd, J=11, 10 Hz, 1H), 3.53 (dd, J=10, 9 Hz, 1H), 3.42 (dd, J= 10, 9 Hz, 1H), 3.29 (td, J=10, 5 Hz, 1H), 3.21 (dd, J=12, 5 Hz, 1H), 2.71 (td, J=10, 5 Hz, 1H), 2.54 (dd, J=12, 10 Hz, 1H), 1.15 (broad s, 1H).

EXAMPLE 41

2,3-diazido-1,5-(butylimino)-1,2,3,5-tetradeoxy-4,6-O-(R-phenylmethylene)-D-glucitol(44)

To a solution of 43 (360 mg, 1.19 mmol) in methanol (10 ml), molecular sieves (4Å, 0.7 g) were added. After stirring for 5 min, butyraldehyde (0.22 ml, 2.4 mol), acetic acid (0.2 ml) and sodium cyanoborohydride (95%, 111 mg, 1.78 mmol) were added. The reaction was stirred at 22° C. for 18 hr, filtered and the residue washed with more methanol. The combined organic fractions were concentrated. The residue was redissolved in ethyl acetate and washed with aqueous potassium carbonate, water and brine. After drying (MgSO$_4$) and concentration, the crude (0.47 g) was chromatographed (silica gel, hexane/ethyl acetate 8/2) to give pure 44 (410 mg, 94%). $^1$H NMR (CDCl$_3$) 7.50 (m, 2H), 7.37 (m, 3H), 5.58 (s, 1H), 4.43 (dd, J=11, 5 Hz, 1H), 3.68 (dd, J=11, 10 Hz, 1H), 3.59 (t, J=9 Hz, 1H), 3.45 (dd, J=10, 9 Hz, 1H), 3.38 (td, J=10, 5 Hz, 1H), 3.07 (dd, J=12, 5 Hz, 1H), 2.53 (dr, J=13, 8 Hz, 1H), 2.41 (ddd, J=10, 9, 5 Hz, 1H), 2.30 (dr, J=13, 7 Hz, 1H), 2.17 (dd, J=12, 10 Hz, 1H), 1.39 (m, 2H), 1.28 (m, 2H), 0.92 (t, J=7 Hz, 3H).

EXAMPLE 42

2,3-diamino-1,5-(butylimino)-1,2,3,5-tetradeoxy-4,6-O-(R-phenylmethylene)-D-glucitol(45)

To a solution of 44 (385 mg, 1.08 mmol) in methanol (25 ml) in a Parr hydrogenation flask, 10% Pd on C (60 mg) was added. The system was sealed, purged with nitrogen (5 times) and hydrogen (5 times) and then pressurized to 5 psi hydrogen. After running the reaction on a shaker for 3.5 hr, the system was vented, purged with nitrogen and filtered. The filtrate was concentrated and the crude (320 mg) was chromatographed (silica gel, ethyl acetate/methanol/ammonium hydroxide 50/50/2.5) to give 45 (240 mg, 73%). Anal calcd. for C$_{17}$H$_{27}$N$_3$O$_2$ 0.25H20, C, 65.88, H, 8.94, N, 13.56 Found C, 65.53, H, 8.99, N, 13.28.

EXAMPLE 43

2,3-diamino-1,5-(butylimino)-1,2,3,5-tetradeoxy-D-glucitol(46)

A solution of 45 (235 mg, 0.77 mmol) in trifluoroacetic acid/water (4/1, 10 ml) was stirred at 22° C. for 18 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/methanol-/ammonium hydroxide 25/75/3), were pooled and concentrated. The water in the fractions was azeotropically removed with toluene to give crude 46 (152 mg) which was rechromatographed (silica gel, ethyl acetate/methanol/ammonium hydroxide 25/75/3) to give pure 46 (72 mg, 43%). Anal calcd. for C$_{10}$H$_{23}$N$_3$O$_2$, C, 55.27, H, 10.67, N, 19.34 Found C, 54.86, H, 10.78, N, 19.00.

EXAMPLE 44

Synthesis of
1,3,5-trideoxy-3-[{2-(dimethylamino)ethyl}amino]-1,5[{(phenylmethoxy)carbonyl}imino]-4,6-O-(R-phenylmethylene)-D-altritol (47)

A solution of epoxide 5 (734 mg, 2 mmol) in N,N-dimethylaminoethylamine (7 ml) was heated at 100° C. for 24 hr. Part of the solvent was removed under reduced pressure and the crude residue was chromatographed (silica gel, methylene chloride/methanol/ammonium hydroxide 90/10/1) to give pure 47 (700 mg, 76%) as an oil. Anal calcd. for C$_{25}$H$_{33}$N$_3$O$_5$, C, 65.91, H, 7.30, N, 9.22 Found C, 65.65, H, 7.45, N, 9.02.

EXAMPLE 45

Synthesis of 3-(butylamino)-1,3,5-trideoxy-1,5-[{(phenylmethoxy)carbonyl}imino]-4,6-O- (R-phenylmethylene)-D-altritol (48 )

A solution of epoxide 5 (200 mg, 0.55 mmol) in butylamine (4 ml) was refluxed for 24 hr. Part of the solvent was removed under reduced pressure and the crude residue was chromatographed (silica gel, hexane/ethyl acetate 70/30) to give pure 48 (117 rag, 70%). mp 104°-6° C., Anal calcd. for C$_{25}$H$_{32}$N$_2$O$_5$, C, 68.16, H, 7.32 , N, 6.36 Found C, 68.04 , H, 7 . 39, N, 6.34.

EXAMPLE 46

Synthesis of 1,3,5-trideoxy-3-[{2-(dimethylamino)ethyl}amino]-1,5-imino-4,6-O-(R-phenylmethylene)-D-altritol (49)

To a solution of 47 (1.78 g, 3.9 mmol) in ethanol (35 ml) in a Parr hydrogenation flask, 4% Pd on C (250 mg) was added. The system was sealed, purged with nitrogen (5 times) and hydrogen (5 times) and then pressurized to 5 psi hydrogen. After running the reaction on a shaker for 5 hr, the system was vented, purged with nitrogen and filtered. The filtrate was concentrated and the crude was crystallized from cyclohexane to give 49 (1.14 g, 91%). mp 100°–2° C., Anal calcd. for $C_{17}H_{27}N_3O_3$, C, 63.53, H, 8.47, N, 13.07 Found C, 63.28, H, 8.59, N, 12.85.

EXAMPLE 47

Synthesis of 3-[{2-(dimethylamino)ethyl}amino]-1,3,5-trideoxy-1,5-imino-D-altritol (50)

A solution of 49 (600 mg, 1.8 mmol) in trifluoroacetic acid/water (4/1, 6 ml) was stirred at 25° C. for 25 hr. The solvent was removed under reduced pressure and the residue was passed through an ion-exchange column [Amberlite, IRA-400 (OH)] prewashed with distilled water until neutral. The basic fractions, as also followed by TLC (silica gel, ethyl acetate/methanol/ammonium hydroxide 25/75/3), were pooled and concentrated. The water in the fractions was azeotropically removed with toluene to give 50 (250 mg, 72%) which was recrystallized from methanol. mp 120°–22° C., Anal calcd. for $C_{10}H_{23}N_3O_3$, C, 51.47, H, 9.93, N, 18.00 Found C, 51.61, H, 9.72, N, 17.81.

EXAMPLE 48

Various illustrative compounds synthesized above were tested for inhibition of visna virus in vitro in a plaque reduction assay (Method A) or for inhibition of HIV-1 in a test which measured reduction of cytopathogenic effect in virus-infected synctium-sensitive Leu-3a-positive CEM cells grown in tissue culture (Method B) as follows:

Method A

Cell and Virus Propagation

Sheep choroid plexus (SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at −70° C.

Plaque Reduction Assay

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5 ml of Medium 199 (M-199) supplemented with 2% lamb serum, 4 mM glutamine, 0.5% agarose and gentamycin was added to each well. Cultures were incubated at 37° C. in a humidified 5% $CO_2$ incubator for 3–4 weeks. To terminate the test; cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 Well Plate Assay

The 96 well plate assay was performed similarly to the plaque assay above with modifications. SCP cells were seeded at $1 \times 10^4$ cells per well in 0.1 ml DME medium. When confluent, the wells were washed with serum free MEM and 25 μl of virus added in M-199 supplemented with 2% lamb serum. After 1 hour, 75 μL of medium containing test compound was added to each well containing virus. After 2–3 weeks incubation the cytopathic effect of the virus was determined by staining with a vital stain. Cell viability was measured by determining stain density using a 96 well plate reader.

Control wells without virus were completed to determine the toxicity of compounds.

Method B

Tissue culture plates were incubated at 37° C. in humidified, 5% $CO_2$ atmosphere and observed microscopically for toxicity and/or cytopathogenic effect (CPE). At 1 hour prior to infection each test article was prepared from the frozen stock, and a 20 μl volume of each dilution (prepared as a 10× concentration) was added to the appropriate wells of both infected and uninfected cells.

On the 9th day post-infection, the cells in each well were resuspended and a 100 μl sample of each cell suspension was removed for use in an MTT assay. A 20 μl volume of a 5 mg/ml solution of 3-(4,5-dimethylthiazol-2-yl)-2,5-diphenyltetrazolium bromide (MTT) was added to each 100 μl cell suspension, and the cells were incubated at 37° C. in 5% $CO_2$ for 4 hours. During this incubation MTT is metabolically reduced by living cells, resulting in the production of a colored formazan product. A 100 μl volume of a solution of 10% sodium dodecyl sulfate in 0.01N hydrochloric acid was added to each sample, and the samples were incubated overnight. The absorbance at 590 nm was determined for each sample using a Molecular Devices $V_{max}$ microplate reader. This assay detects drug-induced suppression of viral CPE, as well as drug cytotoxicity, by measuring the generation of MTT-formazan by surviving cells.

Assays were done in 96-well tissue culture plates. CEM cells were treated with polybrene at-a concentration of 2 μg/ml, and an 80 μl volume of cells ($1 \times 10^4$ cells) was dispensed into each well. A 100 μl volume of each test article dilution (prepared as a 2× concentration) was added to 5 wells of cells, and the cells were incubated at 37° C. for 1 hour. A frozen culture of HIV-1, strain HTVL-III$_B$, was diluted in culture medium to a concentration of $5 \times 10^4$ TCID$_{50}$ per ml, and a 20 μl volume (containing $10^3$ TCID$_{50}$ of virus) was added to 3 of the wells for each test article concentration. This resulted in a multiplicity of infection of 0.1 for the HIV-1 infected samples. A 20 μl volume of normal culture medium was added to the remaining wells to allow evaluation of cytotoxicity. Each plate contained 6 wells of untreated, uninfected, cell control samples and 6 wells of untreated, infected, virus control samples.

Tables 2–6, below, set forth the results of the assay for illustrative compounds prepared in the foregoing Examples in Method A: These results are stated in terms of % Plaque Reduction (mM concentration).

TABLE 2

Anti-Viral Activity of 2-Azido Analogs

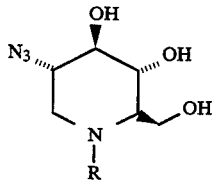

| Compound | R | Visna % Plaque Redn (Conc) |
|---|---|---|
| 12 | H | 76 (0.1 mM) |
| 13 | n-Bu | 78 (0.1 mM) |
| 14 | $CH_2CH(Et)_2$ | 67 (0.1 mM) |
| 15 | $(CH_2)_3CF_3$ | 41 (1 mM) |

TABLE 3

Anti-Viral Activity of 2-Amino Analogs

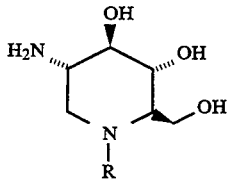

| Compound | R | Visna % Plaque Redn (Conc) |
|---|---|---|
| 20 | H | 91 (0.1 mM) |
| 21 | n-Bu | 66 (0.1 mM) |
| 22 | $CH_2CH(Et)_2$ | >1 mm |
| 23 | $(CH_2)_3CF_3$ | 9 (1 mM) |

TABLE 4

Anti-Viral Activity of 2-Substituted Analogs

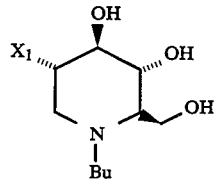

| Compound | $X_1$ | Visna % Plaque Redn (Conc) |
|---|---|---|
| 13 | $N_3$ | 78 (0.1 mM) |
| 21 | $NH_2$ | 66 (0.1 mM) |
| 28 | $NMe_2$ | 41 (0.1 mM) |
| 29 | NHMe | 25 (0.1 mM) |
| 30 | NHCOPr | 20 (0.1 mM) |
| 31 | NHCOPr (Per Butyr) | 29 (0.1 mM) |

TABLE 5

Anti-Viral Activity of C-2 & C-3 Substituted Analogs

TABLE 5-continued

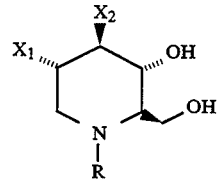

| Compound | $X_1, X_2$ | Visna % Plaque Redn (Conc) |
|---|---|---|
| 37 (R = H) | $X_1$ = H, $X_2$ = $NH_2$ | 30 (1 mM) |
| 46 (R = Bu) | $X_1$ = $X_2$ = $NH_2$ | 3 (1 mM) |

TABLE 6

Anti-Viral Activity of 3-amino Analog

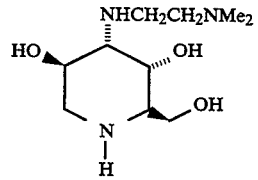

| Compound | Visna % Plaque Redn (Conc) |
|---|---|
| 50 | 38 (1 mM) |

Compound (50) also effectively inhibited both α- and β-glucosidase enzymes 22% at 1 mM concentration as determined in conventional assays for these enzymes described in U.S. Pat. No. 4,973,602.

The antiviral agents described herein can be used for administration to a mammalian host infected with a virus, e.g. visna virus or in vitro to the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. A compound of the formula

39
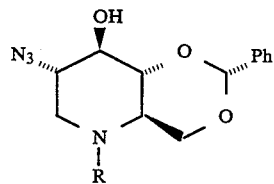
wherein R=H, n—C$_4$H$_9$, CH$_2$CH(C$_2$H$_5$)$_2$ and (CH$_2$)$_3$CF$_3$.
2. A compound of the formula
40
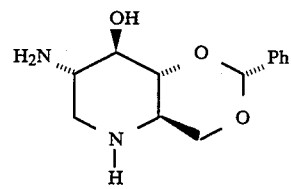
wherein R=H, n—C$_4$H$_9$, CH$_2$CH(C$_2$H$_5$)$_2$ and (CH$_2$)$_3$CF$_3$.
* * * * *